(12) United States Patent
Zhu et al.

(10) Patent No.: US 8,173,604 B2
(45) Date of Patent: May 8, 2012

(54) INHIBITION OF SKP2-CYCLIN A INTERACTION

(75) Inventors: Liang Zhu, Ardsley, NY (US); Peng Ji, Watertown, MA (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 470 days.

(21) Appl. No.: 12/226,935

(22) PCT Filed: May 23, 2007

(86) PCT No.: PCT/US2007/012277
§ 371 (c)(1),
(2), (4) Date: Jul. 24, 2009

(87) PCT Pub. No.: WO2007/139820
PCT Pub. Date: Dec. 6, 2007

(65) Prior Publication Data
US 2010/0075892 A1     Mar. 25, 2010

Related U.S. Application Data

(60) Provisional application No. 60/802,973, filed on May 24, 2006.

(51) Int. Cl.
*A61K 38/10*     (2006.01)
*A61K 38/16*     (2006.01)

(52) U.S. Cl. .................................................. 514/21.4
(58) Field of Classification Search .................. None
See application file for complete search history.

(56) References Cited

U.S. PATENT DOCUMENTS 5,981,702 A      11/1999  Zhang et al.
2002/0123082 A1*  9/2002  Pagano ................... 435/7.23

OTHER PUBLICATIONS

Llsztwan et al. Association of human CUL-1 and ubiquitin-conjugating enzyme CDC43 with the F-box protein p45SPK2: evidence for evolutionary conservation in the subunit composition of the CDC34-SCF pathway. The EMBO Journal. 1998. vol. 17 No. 2 pp. 368-383.*
Yam et al. Cyclin A in cell cycle control and cancer. Review. Cell Mol Life Sci. 2002. vol. 59, pp. 1317-1326.*
The International Search Report for PCT Application No. PCT/US2007/012277.
The Written Opinion for PCT Application No. PCT/US2007/012277.

* cited by examiner

*Primary Examiner* — Marcela M Cordero Garcia
(74) *Attorney, Agent, or Firm* — Amster Rothstein & Ebenstein LLP

(57) ABSTRACT

Methods of killing a cancer cell are provided. Also provided are methods of treating a subject having a cancer. Additionally, compounds are provided that comprise a peptide from about 18 to about 100 amino acids or peptidomimetics comprising the sequence of SEQ ID NO:1. Additionally provided are methods of screening an agent for the ability to kill a cancer cell.

6 Claims, 15 Drawing Sheets

SEQUENCE LISTING

<160> NUMBER OF SEQ IDS: 18

<210> SEQ ID NO 1
<211> LENGTH: 18
<212> TYPE: PRT
<213> ORGANISM: Artificial
<220> FEATURE:
<223> OTHER INFORMATION: combination of 4060 peptide and metazoan
      peptides analogous to 4060 peptide
<220> FEATURE:
<221> NAME/KEY: PEPTIDE
<222> LOCATION: (1)..(1)
<223> OTHER INFORMATION: X = lysine or glutamic acid
<220> FEATURE:
<221> NAME/KEY: PEPTIDE
<222> LOCATION: (2)..(2)

-continued

```
<223> OTHER INFORMATION: X = threonine or lysine
<220> FEATURE:
<221> NAME/KEY: PEPTIDE
<222> LOCATION: (3)..(3)
<223> OTHER INFORMATION: X = serine or leucine
<220> FEATURE:
<221> NAME/KEY: PEPTIDE
<222> LOCATION: (4)..(4)
<223> OTHER INFORMATION: X = glutamic acid or glutamine
<220> FEATURE:
<221> NAME/KEY: PEPTIDE
<222> LOCATION: (5)..(5)
<223> OTHER INFORMATION: X = isoleucine or leucine
<220> FEATURE:
<221> NAME/KEY: PEPTIDE
<222> LOCATION: (7)..(7)
<223> OTHER INFORMATION: X = serine or alanine
<220> FEATURE:
<221> NAME/KEY: PEPTIDE
<222> LOCATION: (8)..(8)
<223> OTHER INFORMATION: X = glycine or glutamine
<220> FEATURE:
<221> NAME/KEY: PEPTIDE
<222> LOCATION: (9)..(9)
<223> OTHER INFORMATION: X = methionine or alanine
<220> FEATURE:
<221> NAME/KEY: PEPTIDE
<222> LOCATION: (10)..(10)
<223> OTHER INFORMATION: X = glycine or lysine
<220> FEATURE:
<221> NAME/KEY: PEPTIDE
<222> LOCATION: (11)..(11)
<223> OTHER INFORMATION: X = valine or arginine
<220> FEATURE:
<221> NAME/KEY: PEPTIDE
<222> LOCATION: (13)..(13)
<223> OTHER INFORMATION: X = alanine, valine or serine
<220> FEATURE:
<221> NAME/KEY: PEPTIDE
<222> LOCATION: (15)..(15)
<223> OTHER INFORMATION: X = glutamic acid, arginine or glycine
<220> FEATURE:
<221> NAME/KEY: PEPTIDE
<222> LOCATION: (16)..(16)
<223> OTHER INFORMATION: X = lysine or serine
<220> FEATURE:
<221> NAME/KEY: PEPTIDE
<222> LOCATION: (17)..(17)
<223> OTHER INFORMATION: X = glutamic acid or aspartic acid
<220> FEATURE:
<221> NAME/KEY: PEPTIDE
<222> LOCATION: (18)..(18)
<223> OTHER INFORMATION: X = glutamic acid, lysine or glycine

<400> SEQUENCE: 1

Xaa Xaa Xaa Xaa Xaa Leu Xaa Xaa Xaa Xaa Xaa Ser Xaa Leu Xaa Xaa
1               5                   10                  15

Xaa Xaa

<210> SEQ ID NO 2
<211> LENGTH: 18
<212> TYPE: PRT
<213> ORGANISM: Artificial
<220> FEATURE:
<223> OTHER INFORMATION: combination of 4060 peptide and vertebrate
      peptides analogous to 4060 peptide
<220> FEATURE:
<221> NAME/KEY: PEPTIDE
<222> LOCATION: (13)..(13)
<223> OTHER INFORMATION: X = alanine or valine
<220> FEATURE:
<221> NAME/KEY: PEPTIDE
<222> LOCATION: (15)..(15)
<223> OTHER INFORMATION: X = glutamic acid or arginine
<220> FEATURE:
<221> NAME/KEY: PEPTIDE
<222> LOCATION: (17)..(17)
```

-continued

```
<223> OTHER INFORMATION: X = glutamic acid or aspartic acid
<220> FEATURE:
<221> NAME/KEY: PEPTIDE
<222> LOCATION: (18)..(18)
<223> OTHER INFORMATION: X = glutamic acid or lysine

<400> SEQUENCE: 2

Lys Thr Ser Glu Leu Leu Ser Gly Met Gly Val Ser Xaa Leu Xaa Lys
1               5                   10                  15

Xaa Xaa

<210> SEQ ID NO 3
<211> LENGTH: 18
<212> TYPE: PRT
<213> ORGANISM: Homo sapiens

<400> SEQUENCE: 3

Lys Thr Ser Glu Leu Leu Ser Gly Met Gly Val Ser Ala Leu Glu Lys
1               5                   10                  15

Glu Glu

<210> SEQ ID NO 4
<211> LENGTH: 21
<212> TYPE: PRT
<213> ORGANISM: Artificial
<220> FEATURE:
<223> OTHER INFORMATION: 4060 peptide with 3 amino acids at C terminus
      as in FIG. 1D

<400> SEQUENCE: 4

Lys Thr Ser Glu Leu Leu Ser Gly Met Gly Val Ser Ala Leu Glu Lys
1               5                   10                  15

Glu Glu Pro Asp Ser
            20

<210> SEQ ID NO 5
<211> LENGTH: 21
<212> TYPE: PRT
<213> ORGANISM: Artificial
<220> FEATURE:
<223> OTHER INFORMATION: mouse analog of SEQ ID NO:4 sequence

<400> SEQUENCE: 5

Lys Thr Ser Glu Leu Leu Ser Gly Met Gly Val Ser Ala Leu Glu Lys
1               5                   10                  15

Glu Glu Val Asp Ser
            20

<210> SEQ ID NO 6
<211> LENGTH: 21
<212> TYPE: PRT
<213> ORGANISM: Artificial
<220> FEATURE:
<223> OTHER INFORMATION: chicken analog of SEQ ID NO:4 sequence

<400> SEQUENCE: 6

Lys Thr Ser Glu Leu Leu Ser Gly Met Gly Val Ser Val Leu Arg Lys
1               5                   10                  15

Asp Lys Leu Gly Asn
            20

<210> SEQ ID NO 7
<211> LENGTH: 21
<212> TYPE: PRT
<213> ORGANISM: Artificial
```

```
<220> FEATURE:
<223> OTHER INFORMATION: Drosophila analog of SEQ ID NO:4 sequence

<400> SEQUENCE: 7

Glu Lys Leu Gln Ile Leu Ala Gln Ala Lys Arg Ser Ser Leu Gly Ser
1               5                   10                  15

Glu Gly Ser Gly Asn
            20

<210> SEQ ID NO 8
<211> LENGTH: 435
<212> TYPE: PRT
<213> ORGANISM: Homo sapiens

<400> SEQUENCE: 8

Met His Val Phe Lys Thr Pro Gly Pro Ala Asp Ala Met His Arg Lys
1               5                   10                  15

His Leu Gln Glu Ile Pro Asp Leu Ser Ser Asn Val Ala Thr Ser Phe
            20                  25                  30

Thr Trp Gly Trp Asp Ser Ser Lys Thr Ser Glu Leu Leu Ser Gly Met
        35                  40                  45

Gly Val Ser Ala Leu Glu Lys Glu Glu Pro Asp Ser Glu Asn Ile Pro
    50                  55                  60

Gln Glu Leu Leu Ser Asn Leu Gly His Pro Glu Ser Pro Pro Arg Lys
65                  70                  75                  80

Arg Leu Lys Ser Lys Gly Ser Asp Lys Asp Phe Val Ile Val Arg Arg
                85                  90                  95

Pro Lys Leu Asn Arg Glu Asn Phe Pro Gly Val Ser Trp Asp Ser Leu
            100                 105                 110

Pro Asp Glu Leu Leu Gly Ile Phe Ser Cys Leu Cys Leu Pro Glu
        115                 120                 125

Leu Leu Lys Val Ser Gly Val Cys Lys Arg Trp Tyr Arg Leu Ala Ser
    130                 135                 140

Asp Glu Ser Leu Trp Gln Thr Leu Asp Leu Thr Gly Lys Asn Leu His
145                 150                 155                 160

Pro Asp Val Thr Gly Arg Leu Leu Ser Gln Gly Val Ile Ala Phe Arg
                165                 170                 175

Cys Pro Arg Ser Phe Met Asp Gln Pro Leu Ala Glu His Phe Ser Pro
            180                 185                 190

Phe Arg Val Gln Asp Met Asp Leu Ser Asn Ser Val Ile Glu Val Ser
        195                 200                 205

Thr Leu His Gly Ile Leu Ser Gln Cys Ser Lys Leu Gln Asn Leu Ser
    210                 215                 220

Leu Glu Leu Arg Leu Ser Asp Pro Ile Val Asn Thr Leu Ala Lys Asn
225                 230                 235                 240

Ser Asn Leu Val Arg Leu Asn Leu Pro Gly Cys Pro Gly Phe Pro Lys
                245                 250                 255

Phe Pro Leu Gln Thr Phe Leu Ser Ser Cys Pro Arg Leu Asp Glu Leu
            260                 265                 270

Asn Leu Ser Trp Cys Phe Asn Phe Thr Glu Lys His Val Gln Val Ala
        275                 280                 285

Val Ala His Val Ser Glu Thr Met Thr Gln Leu Asn Leu Ser Gly Tyr
    290                 295                 300

Arg Lys Asn Leu Gln Lys Ser Asp Leu Ser Thr Leu Val Arg Arg Cys
305                 310                 315                 320

Pro Asn Leu Val His Leu Asp Leu Ser Asn Ser Val Met Leu Lys Asn
```

```
                        325                 330                 335
Asp Cys Phe Gln Glu Phe Ser Gln Leu Asn Tyr Leu Gln His Leu Ser
            340                 345                 350

Leu Ser Arg Cys Tyr Asp Ile Ile Pro Glu Thr Leu Glu Leu Gly
        355                 360                 365

Glu Ile Pro Thr Leu Lys Thr Leu Gln Val Phe Gly Ile Val Pro Asp
    370                 375                 380

Gly Thr Leu Gln Leu Leu Lys Glu Ala Leu Pro His Leu Gln Ile Asn
385                 390                 395                 400

Cys Ser His Phe Thr Thr Ile Ala Arg Pro Thr Ile Gly Asn Lys Lys
                405                 410                 415

Asn Gln Glu Ile Trp Gly Ile Lys Cys Arg Leu Thr Leu Gln Lys Pro
            420                 425                 430

Ser Cys Leu
        435

<210> SEQ ID NO 9
<211> LENGTH: 8
<212> TYPE: PRT
<213> ORGANISM: Artificial
<220> FEATURE:
<223> OTHER INFORMATION: peptide RxL

<400> SEQUENCE: 9

Ser Ala Cys Arg Asn Leu Phe Gly
1               5

<210> SEQ ID NO 10
<211> LENGTH: 18
<212> TYPE: PRT
<213> ORGANISM: Artificial
<220> FEATURE:
<223> OTHER INFORMATION: peptide 4060AAAA

<400> SEQUENCE: 10

Lys Thr Ser Glu Ala Ala Ser Gly Met Gly Val Ala Ala Ala Glu Lys
1               5                   10                  15

Glu Glu

<210> SEQ ID NO 11
<211> LENGTH: 8
<212> TYPE: PRT
<213> ORGANISM: Artificial
<220> FEATURE:
<223> OTHER INFORMATION: peptide LDL

<400> SEQUENCE: 11

Pro Val Lys Arg Arg Leu Asp Leu
1               5

<210> SEQ ID NO 12
<211> LENGTH: 19
<212> TYPE: DNA
<213> ORGANISM: Homo sapiens

<400> SEQUENCE: 12
ccttagacct cacaggtaa                                              19

<210> SEQ ID NO 13
<211> LENGTH: 19
<212> TYPE: DNA
<213> ORGANISM: Homo sapiens
```

-continued

```
<400> SEQUENCE: 13
cagtcggtgc tatgatata                                              19

<210> SEQ ID NO 14
<211> LENGTH: 19
<212> TYPE: DNA
<213> ORGANISM: Artificial
<220> FEATURE:
<223> OTHER INFORMATION: negative control

<400> SEQUENCE: 14
gttacaaagc agaagttaa                                              19

<210> SEQ ID NO 15
<211> LENGTH: 30
<212> TYPE: PRT
<213> ORGANISM: Artificial
<220> FEATURE:
<223> OTHER INFORMATION: TAT-4060

<400> SEQUENCE: 15

Tyr Gly Arg Lys Lys Arg Arg Gln Arg Arg Gly Lys Thr Ser Glu
1               5                   10                  15

Leu Leu Ser Gly Met Gly Val Ser Ala Leu Glu Lys Glu Glu
            20                  25                  30

<210> SEQ ID NO 16
<211> LENGTH: 30
<212> TYPE: PRT
<213> ORGANISM: Artificial
<220> FEATURE:
<223> OTHER INFORMATION: TAT-4060AAAA

<400> SEQUENCE: 16

Tyr Gly Arg Lys Lys Arg Arg Gln Arg Arg Gly Lys Thr Ser Glu
1               5                   10                  15

Ala Ala Ser Gly Met Gly Val Ala Ala Ala Glu Lys Glu Glu
            20                  25                  30

<210> SEQ ID NO 17
<211> LENGTH: 20
<212> TYPE: PRT
<213> ORGANISM: Artificial
<220> FEATURE:
<223> OTHER INFORMATION: TAT-LDL

<400> SEQUENCE: 17

Tyr Gly Arg Lys Lys Arg Arg Gln Arg Arg Gly Pro Val Lys Arg
1               5                   10                  15

Arg Leu Asp Leu
            20

<210> SEQ ID NO 18
<211> LENGTH: 23
<212> TYPE: PRT
<213> ORGANISM: Artificial
<220> FEATURE:
<223> OTHER INFORMATION: TAT-Umt

<400> SEQUENCE: 18

Tyr Gly Arg Lys Lys Arg Arg Gln Arg Arg Gly Glu Thr Asp His
1               5                   10                  15

Gln Tyr Leu Ala Glu Ser Ser
            20
```

US 8,173,604 B2

INHIBITION OF SKP2-CYCLIN A INTERACTION

CROSS-REFERENCE TO RELATED APPLICATION

This is a U.S. national phase of PCT Application No. PCT/US2007/012277, filed May 23, 2007, which claims the benefit of U.S. Provisional Application No. 60/802,973, filed May 24, 2006.

STATEMENT REGARDING FEDERALLY SPONSORED RESEARCH OR DEVELOPMENT

The invention was made with government support under Grant Nos. R01CA87566 and R01DK58640 awarded by the National Institutes of Health. The government has certain rights in the invention

BACKGROUND OF THE INVENTION (1) Field of the Invention

The present invention generally relates to cancer treatments. More specifically, the invention is directed to methods of inhibiting the Skp2-cyclin A interaction.

(2) Description of the Related Art

Skp2 is one of the founding members of the F-box protein family that serves as the ubiquitylation substrate recruiting subunit of the SCF$^{Skp2}$Roc1 complex (Bai et al., 1996). The best-established substrate of Skp2 is the CKI p27 (Carrano et al., 1999; Sutterluty et al., 1999; Tsvetkov et al., 1999), although Skp2 can also promote ubiquitylation and degradation of other proteins including the p27 family members p21 (Bornstein et al., 2003) and p57 (Kamura et al., 2003). Since p27 is a negative regulator of cell proliferation, the p27 ubiquitylation activity of Skp2 suggested that it is a proliferation-stimulating protein. Indeed, Skp2 exhibits proliferation-stimulating activity in various experimental assays and is found overexpressed in various human cancers (Nakayama and Nakayama, 2005).

Another property of Skp2 is its interaction with cyclin A. In fact, Skp2 was first identified and cloned as a cyclin A associated protein in transformed cells (Xiong et al., 1993), and Skp2 associated with both cyclin A and Skp1 in stoichiometric amounts (Zhang et al., 1995). If protein-protein interactions and the efficiencies of interactions are indications to protein functions, these early findings should suggest that Skp2-cyclin A interaction is an important aspect of Skp2 function. Surprisingly however, prior to the present work, very little has been learned about the Skp2-cyclin A interaction more than ten years after its identification. Mapping of cyclin A interacting sequences of Skp2 was uncertain and the functional significance of Skp2-cyclin A interaction was controversial (see below). The role of Skp2 as a proliferation-stimulating protein has been exclusively attributed to p27 ubiquitylation and degradation.

SUMMARY OF THE INVENTION

The invention is directed to methods of killing a cancer cell. The methods comprise contacting the cell with a compound that inhibits binding of Skp2 with cyclin A in the cell.

The invention is also directed to methods of treating a subject having a cancer. The methods comprise administering to the subject a compound that inhibits binding of Skp2 with cyclin A in an amount sufficient to treat cancer in the subject.

Additionally, the invention is directed to compounds comprising a peptide from about 18 to about 100 amino acids or peptidomimetics comprising the sequence of SEQ ID NO:1.

The invention is further directed to methods of screening an agent for the ability to kill a cancer cell. The methods comprise determining whether the agent inhibits Skp2-cyclin A binding, wherein an agent that inhibits Skp2-cyclin A binding could kill the cancer cell.

DETAILED DESCRIPTION OF THE INVENTION

Figure 1:
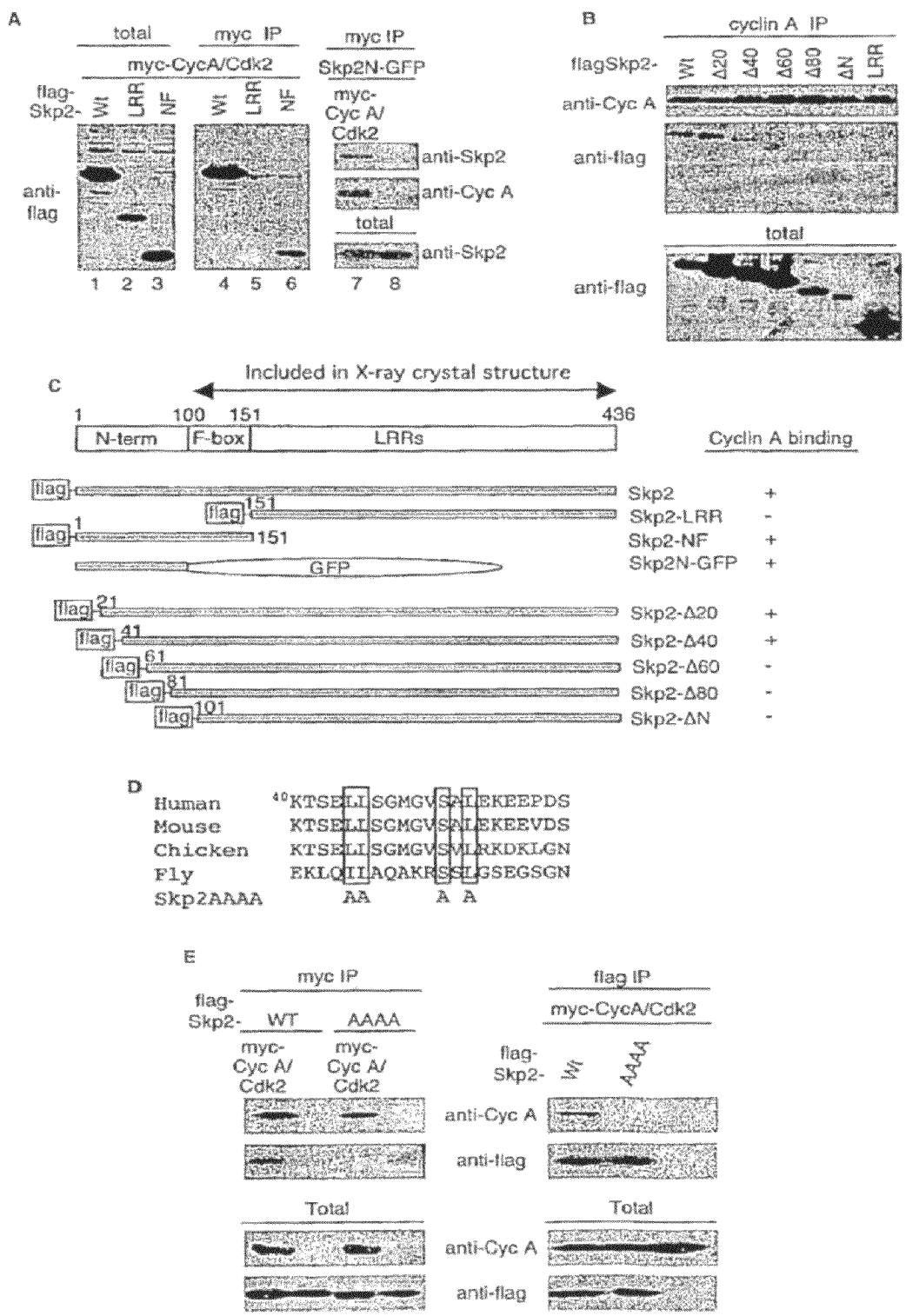
FIG. 1 is diagrams and photographs of western blots showing the identification of Skp2 sequences required for binding cyclin A. Panels A and B show western blots where 293T cells were first transfected with various expression vectors as indicated. Immunoprecipitation (IP)-Western blot assays were performed with extracts of transfected cells. Panel C is a schematic drawing of Skp2 domain structure, various mutants, and their ability to bind cyclin A as determined in Panels A and B. Panel D shows the alignment of the human Skp2 sequence from amino acid residue 40 to 60 (SEQ ID NO:4) with corresponding sequences of Skp2 orthologs in different species (SEQ ID NO:5-7—mouse, chicken and Drosophila, respectively). Identical residues are boxed and were mutated to alanine in Skp2AAAA. Panel E shows the results of an IP-Western assay with transfected 293T cell extracts as described in Panel A and B.

Accordingly, the inventors have discovered the binding sites of the Skp2-cyclin A interaction. They have also identified a peptide from Skp2 that inhibits the Skp2-cyclin A interaction. Treatment of cancer cells with the peptide causes the cancer cells' death. See Examples.

Thus, the invention is directed to methods of killing a cancer cell. The methods comprise contacting the cell with a compound that inhibits binding of Skp2 with cyclin A in the cell.

The compound in these methods is not narrowly limited to any particular type of molecule, and includes macromolecules such as proteins, peptides, or nucleic acids (e.g., aptamers), and small organic molecules (i.e., less than about 1000 Da). It is anticipated that the compound binds to either Skp2 or cyclin A. As established in the Examples, cyclin A interacts with human Skp2 (SEQ ID NO:8) at the region around residues 40-57, provided here as SEQ ID NO:3. Thus, a compound designed to bind to either Skp2 or cyclin A at the regions of interaction would be expected to inhibit the Skp2-cyclin A interaction. Methods for designing and preparing both macromolecules and small organic molecules to bind at those regions are known.

The Examples establish that the 4060 peptide (SEQ ID NO:3), corresponding to residues 40-57 of the human Skp2 (SEQ ID NO:8), inhibits the cyclin A-Skp2 interaction. It is expected that corresponding peptides from other metazoans would also be effective in inhibiting the Skp 2-cyclin A interaction in those organisms. Examples of such analogous peptides, with 3 additional amino acids, are provided herein as SEQ ID NO:5 (from mouse), SEQ ID NO:6 (from chicken) and SEQ ID NO:7 (from *Drosophila*). A comparison of those sequences with the 4060 peptide (Example 1) shows that some residues are highly conserved and others show variation among the metazoan sequences. Such a comparison reveals likely regions of the peptide that are crucial to the Skp2-cyclin A interaction, as confirmed in Example 1, where the 4060 peptide is shown to lose its ability to prevent the Skp2-cyclin A interaction when the three leucine and the glutamic acid residues at positions 5, 6, 12 and 14 (SEQ ID NO:3) are replaced by alanine. Since the other residues show considerable variation among the metazoans, it is expected that peptides with amino acids replaced at any of these residues with analogous resides from a different metazoan would retain the ability to inhibit the Skp2-cyclin A interaction. Additionally, a compound comprising such peptides, e.g., as part of a larger peptide, or having additional moieties (e.g., a fluorescent moiety) would also be expected to inhibit the Skp2-cyclin A interaction.

Thus, the compound in the invention methods can comprise a peptide from about 18 to about 100 amino acids or peptidomimetics comprising the sequence of SEQ ID NO:1, which represents the combination of the 4060 peptide with the disclosed metazoan analogs to the 4060 peptide from mouse, chicken and *Drosophila* (i.e., the combination of residues 1-18 of SEQ ID NO:4-7). Preferably, the compound comprises a peptide from about 18 to about 100 amino acids or peptidomimetics comprising the sequence of SEQ ID NO:2, which represents the combination of the 4060 peptide with the disclosed vertebrate analogs to the 4060 peptide from mouse and chicken (i.e., the combination of residues 1-18 of SEQ ID NO:4-6). Most preferably, the compound comprises, or consists of, a peptide from about 18 to about 100 amino acids or peptidomimetics comprising the sequence of SEQ ID NO:3 (the 4060 peptide).

It is also preferred that the peptide is homologous to a portion of a mammalian Skp2 protein, wherein the mammalian Skp2 protein is at least 80%, or 90%, or 95%, or 99% identical to SEQ ID NO:8. More preferably, the peptide is homologous to a portion of a human Skp2 protein having the amino acid sequence of SEQ ID NO:8.

The compound can also consist of the peptide from about 18 to about 100 amino acids or peptidomimetics comprising the sequence of SEQ ID NO:1. Preferably, the peptide comprises the sequence of SEQ ID NO:2, more preferably SEQ ID NO:3. Most preferably, the compound consists of the amino acid sequence of SEQ ID NO:3.

Where the compound of these methods comprises a peptide, the peptide preferably has less than about 50 amino acids or peptidomimetics, more preferably less than about 30 amino acids or peptidomimetics.

These methods should be effective in killing any cancer cell. Preferably, the cancer cell is of a glioblastoma, a carcinoma, a lung cancer, a leukemia, a melanoma, an oral cancer, a colorectal cancer, a breast cancer, a hepatoma, an ovarian cancer, a prostate cancer, a lymphoma, or a pituitary cancer. Most preferably, the cancer cell is in a living human.

The invention is also directed to methods of treating a subject having a cancer. The methods comprise administering to the subject a compound that inhibits binding of Skp2 with cyclin A in an amount sufficient to treat cancer in the subject.

The compound in these methods should be formulated in a pharmaceutically acceptable excipient. By "pharmaceutically acceptable" it is meant a material that (i) is compatible with the other ingredients of the composition without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include, without limitation, any of the standard pharmaceutical carriers such as phosphate buffered saline solutions, water, emulsions such as oil/water emulsions, microemulsions, and the like.

The above-described compounds can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compounds can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the compound, in a pharmaceutical composition, into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the mammal a therapeutically effective amount of the compound. As used herein, nasally administering or nasal administration includes administering the compound to the mucous membranes of the nasal passage or nasal cavity of the patient. As used herein, pharmaceutical compositions for nasal administration of the compound include therapeutically effective amounts of the compound prepared by well-known methods to be administered, for example, as a nasal spray, nasal drop, suspension, gel, ointment, cream or powder. Administration of the compound may also take place using a nasal tampon or nasal sponge.

Where the compound is administered peripherally such that it must cross the blood-brain barrier, the compound is preferably formulated in a pharmaceutical composition That enhances the ability of the compound to cross the blood-brain barrier of the mammal. Such formulations are known in the art and include lipophilic compounds to promote absorption. Uptake of non-lipophilic compounds can be enhanced by combination with a lipophilic substance. Lipophilic substances that can enhance delivery of the compound across the nasal mucus include but are not limited to fatty acids (e.g., palmitic acid), gangliosides (e.g., GM-1), phospholipids (e.g., phosphatidylserine), and emulsifiers (e.g., polysorbate 80), bile salts such as sodium deoxycholate, and detergent-like substances including, for example, polysorbate 80 such as Tween™, octoxynol such as Triton™ X-100, and sodium tauro-24,25-dihydrofusidate (STDHF). See Lee et al., Biopharm., April 1988 issue:3037.

In particular embodiments of the invention, the compound is combined with micelles comprised of lipophilic substances. Such micelles can modify the permeability of the nasal membrane to enhance absorption of the compound. Suitable lipophilic micelles include without limitation gangliosides (e.g., GM-1 ganglioside), and phospholipids (e.g., phosphatidylserine). Bile salts and their derivatives and detergent-like substances can also be included in the micelle formulation. The compound can be combined with one or several types of micelles, and can further be contained within the micelles or associated with their surface.

Alternatively, the compound can be combined with liposomes (lipid vesicles) to enhance absorption. The compound can be contained or dissolved within the liposome and/or associated with its surface. Suitable liposomes include phospholipids (e.g., phosphatidylserine) and/or gangliosides (e.g., GM-1). For methods to make phospholipid vesicles, see for example, U.S. Pat. No. 4,921,706 to Roberts et al., and U.S. Pat. No. 4,895,452 to Yiournas et al. Bile salts and their derivatives and detergent-like substances can also be included in the liposome formulation.

For these methods, the compound preferably comprises a peptide from about 18 to about 100 amino acids or peptidomimetics comprising the sequence of SEQ ID NO:1. More preferably, the compound comprises a peptide from about 18 to about 100 amino acids or peptidomimetics comprising the sequence of SEQ ID NO:2. In the most preferred embodiments, the compound comprises a peptide from about 18 to about 100 amino acids or peptidomimetics comprising the sequence of SEQ ID NO:3.

It is also preferred that the peptide is homologous to a portion of a mammalian Skp2 protein, wherein the mammalian Skp2 protein is at least 80%, or 90%, or 95%, or 99% identical to SEQ ID NO:8. More preferably, the peptide is homologous to a portion of a human Skp2 protein having the amino acid sequence of SEQ ID NO:8.

The compound can also consist of the peptide from about 18 to about 100 amino acids or peptidomimetics comprising the sequence of SEQ ID NO:1. Preferably, these peptides comprises the sequence of SEQ ID NO:2, more preferably SEQ ID NO:3. The peptide can also consist of SEQ ID NO:3 or SEQ ID NO:4.

Where the compound of these methods comprises a peptide, the peptide preferably has less than about 50 amino acids or peptidomimetics, more preferably less than about 30 amino acids or peptidomimetics.

These methods are not limited to any particular cancer. Preferably, the cancer is a glioblastoma, a carcinoma, a lung cancer, a leukemia, a melanoma, an oral cancer, a colorectal cancer, a breast cancer, a hepatoma, an ovarian cancer, a prostate cancer, a lymphoma, or a pituitary cancer.

Additionally, the invention is directed to compounds comprising a peptide from about 18 to about 100 amino acids or peptidomimetics comprising the sequence of SEQ ID NO:1. Preferably, the compound comprises a peptide from about 18 to about 100 amino acids or peptidomimetics comprising the sequence of SEQ ID NO:2. In the most preferred embodiments, the compound comprises a peptide from about 18 to about 100 amino acids or peptidomimetics comprising the sequence of SEQ ID NO:3.

It is also preferred that the peptide is homologous to a portion of a mammalian Skp2 protein, wherein the mammalian Skp2 protein is at least 80%, or 90%, or 95%, or 99% identical to SEQ ID NO:8. More preferably, the peptide is homologous to a portion of a human Skp2 protein having the amino acid sequence of SEQ ID NO:8.

The compound can consist of a peptide from about 18 to about 100 amino acids or peptidomimetics comprising the sequence of SEQ ID NO:1. Here, the peptide preferably comprises the sequence of SEQ ID NO:2, more preferably SEQ ID NO:3. The compound can also consist of SEQ ID NO:3 or SEQ ID NO:4.

The invention is further directed to methods of screening an agent for the ability to kill a cancer cell. The methods comprise determining whether the agent inhibits Skp2-cyclin A binding, wherein an agent that inhibits Skp2-cyclin A binding could kill the cancer cell. Although many, if not most agents that inhibit Skp2-cyclin A binding would be expected to kill the cancer cell, it is preferred that any agents that inhibit Skp2-cyclin A binding are further tested for their ability to kill the cancer cell, e.g., by the methods described in the Examples.

These methods are not limited to any particular means for determining whether the agent inhibits Skp2-cyclin A binding. In one aspect, this determination is made by (a) combining the agent with the Skp2 and cyclin A under conditions where the Skp2 and cyclin A bind in the absence of the agent, and (b) determining whether the Skp2 and cyclin A bind. See, e.g., Examples. In another aspect, this determination is made by (a) combining the agent with a cyclin A and a compound comprising a peptide from about 18 to about 100 amino acids or peptidomimetics comprising the sequence of SEQ ID NO:1 under conditions where the compound binds to the cyclin A in the absence of the agent, and (b) determining whether the compound binds to the cyclin A, wherein an agent inhibits Skp2-cyclin A binding if the agent causes a reduction in binding of the compound to the cyclin A. The peptide here preferably comprises the sequence of SEQ ID NO:2. More preferably, the peptide comprises the sequence of SEQ ID NO:3. The peptide can also consist of the sequence of SEQ ID NO:3 or SEQ ID NO:4.

One way of determining whether the compound binds to the cyclin A is by using a compound that is labeled with a detectable moiety, such as a fluorescent moiety or a radioactive moiety. The labeling of the compounds and formulation of precise execution of these methods can be prepared by the skilled artisan without undue experimentation.

The agent for these methods can be any chemical, including a macromolecule such as a peptide (e.g., the 4060 peptide) or a nucleic acid (e.g., an aptamer), an inorganic compound, or an organic compound less than 1000 Daltons. Preferably, the agent comprises a peptide from about 18 to about 100 amino acids or peptidomimetics comprising the sequence of SEQ ID NO:1. These compounds are more preferably less than about 50 amino acids or peptidomimetics.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1

Skp2 Contains a Novel Cyclin A Binding Domain that Directly Protects Cyclin A from Inhibition by p27

This example is substantially published as Ji et al., 2006.

Example Summary

Skp2 is well known as the F-box protein of the SCF$^{Skp2}$Roc1 complex targeting p27 for ubiquitylation. Skp2 also binds cyclin A, but the mechanism and significance of this interaction remain unknown. Here, data is presented establishing that the Skp2-cyclin A interaction is mediated by novel interaction sequences on both Skp2 and cyclin A, distinguishing it from the well-known RxL-HP interaction between cyclins and cyclin-binding proteins. The Skp2-cyclin A interaction is separable from Skp2's ability to mediate p27 ubiquitylation, but can directly protect cyclin A/Cdk2 from inhibition by p27 through competitive binding. A peptide replica identified from Skp2 can block the Skp2-cyclin A interaction but not the p27-cyclin A interaction and can therefore inhibit Skp2's ability to protect cyclin A from inhibition by p27. Point mutations in the most conserved residues of the cyclin A binding domain of Skp2 compromise the proliferation-stimulating activity of Skp2 without affecting its ability to cause degradation of cellular p27 and p21. These findings reveal a new functional mechanism of Skp2 and a new regulatory mechanism of cyclin A.

Introduction

In this study, a Skp2-cyclin A interaction is identified. That interaction is a novel type of interaction between cyclin A and its binding proteins. Our investigation of the significance of the Skp2-cyclin A interaction reveals a new functional mechanism of Skp2 and a new regulatory mechanism of cyclin A.

Materials and Methods

Plasmids, antibodies, and peptides. Skp2, Skp2N, and p27 cDNAs were cloned into pGEX-2T. GST-p21 and GST-E2F1 were gifts from Anindya Dutta and Bill Kaelin, respectively. GST-Skp2N-AA45 and GST-Skp2N-AAA53 were generated using the QuickChange kit from Stratagene. GST moiety was cleaved off GST fusion proteins (GST-p27, GST-Skp2N, and GST-Skp2N-AA45) by thrombin for certain experiments. Myc tagged cyclin A and mutant derivatives were generated by PCR. Various cDNAs were cloned under CMV promoter in lenti-CMV-GFP replacing GFP (Follenzi et al., 2002). Other plasmids were described previously (Ji et al., 2004).

Antibodies to myc (9E10), Cdk2 (M-2 and D-12), p53 (DO-1), p21 (C-19), cyclin A (BF683 and C-19), cyclin E (C-19), cyclin D (72-13G), Cdk4 (H-303), Cul1 (H-213) were from Santa Cruz. Anti-Flag (F7425 and F3165) were from Sigma. Anti-p27 was from Pharmingen. Anti-Skp2 (51-1900 and 32-3300) was from Zymed. Peptide RxL (SACRNLFG) (SEQ ID NO:9), 4060 (KTSELLSGMGVSALEKEE) (SEQ ID NO:4), 4060AAAA (KTSEAASGMGVAAAEKEE) (SEQ ID NO:10) were from GenScript.

Cell culture, transfection, lentivirus production and infection. Cell lines U2OS, HeLa, and 293T were maintained in standard conditions. Transfection was performed with standard calcium phosphate protocol. To generate lentivirus stocks, 293T cells were transfected with various lentivirus vectors and packaging vectors (pMDLg/pRRE, pRSV-REV, and pMD2-VSVG) (Follenzi et al., 2002). Cell culture media at 48 hours post-transfection were either used directly or after concentration for infection of U2OS cells at >90% efficiency.

Drug treatment and various routine assays. Actinomycin D (Sigma) treatment was for 20-22 hours at 180 nM. To arrest HeLa cells in mitotic phase, cells were treated with 100 ng/ml nocodazole (Sigma) for 16-17 hours. Western blotting, immunoprecipitation, indirect immunofluorescence, and flow cytometry analysis to determine cell cycle profiles were all performed with standard protocols and as described previously (Ji et al., 2004).

GST pull down, p27 ubiquitylation assay, and cyclin A kinase assay. GST fusion proteins were purified on GSH-beads (Amersham), which were then incubated with transfected cell extracts for 1 hour in 4° C. with rocking. The beads were washed three times with lysis buffer (25 mM Hepes pH 7.6, 100 mM KCl, 0.1 mM EDTA, 10 mM MgCl$_2$, 0.1% NP-40, 10% glycerol, 1 mM DTT) before analysis by SDS-PAGE and Western blotting.

In vitro p27 ubiquitylation assay was performed as described (Ji et al., 2004). Briefly, 293T cells were transfected with CMV expression vectors for flag-Skp2 (wild-type or mutants), myc-Roc1, Cul-1, and Skp-1; and the SCF$^{Skp2}$-Roc1 complex was immuno-purified with anti-flag. The immuno-complexes were washed three times in 1× Ub assay buffer and the Ub reaction was performed by adding the following to the beads in 1× Ub buffer (20 mM HEPES pH 7.2, 10 mM MgCl$_2$, 1 mM DTT): 250 ng of phosphorylated purified p27, 1×ERS, 1 µg each E1 and E2(Cdc34) (Boston Biochem), 10 µg ubiquitin (Sigma), 1 µM ubiquitin-aldehyde, 0.2 mM MG132, 10 ng purified Cks1 (provided by Michelle Pagano), and 1 µM okadaic acid. Reaction mixtures were incubated at 30° C. for 2 hours. Following incubation, p27 was immunoprecipitated from the reaction with polyclonal anti-p27 antibody, resolved by SDS-PAGE, and Western blotted with a monoclonal anti-p27 antibody.

Cyclin A/Cdk2 kinase assays were performed as described previously (Ji et al., 2004). Both immuno-purified myc-cyclin A/Cdk2 on beads and GST-purified and eluted GST-cyclin A/Cdk2 (baculovirus vectors for GST-cyclin A and Cdk2 were provided by Brian Dynlacht) were used. The amounts of purified proteins were determined by comparing them with known amounts of standard proteins in Coomassie blue stained gels. Phosphorylation of GST-Rb-C was quantified with the ImageQuant software. The Ki of various proteins was determined by non-linear least squares analysis. To determine the amounts of various proteins in synchronized HeLa cells, extracts representing $7.5 \times 10^4$ HeLa cells were resolved with known amounts of purified proteins and compared in the same Western blots. Actual amounts of proteins in $7.5 \times 10^4$ HeLa cells were then determined (for example, the amounts of p27, Skp2, and cyclin A in $7.5 \times 10^4$ HeLa cells were determined to be about 0.1, 0.2, and 0.1 pmoles, respectively, at 14 hours post-replating; and about 0.01, 0.1, and 1.0 pmoles, respectively, at 19 hours post-replating). Various molar ratios were then calculated and shown in FIG. 7G.

Results

Identification of a novel cyclin A binding motif in the Skp2 N-terminus. Mapping of cyclin A binding sequences on Skp2 has been attempted previously with discrepant results (Lisztwan et al., 1998; Yam et al., 1999) (also see Discussion). Guided by the Skp2 crystal structure (Schulman et al., 2000), the full-length Skp2 protein was divided at residue 150 (the NF and LRR fragments shown in FIG. 1C) without disrupting α-helices or β-sheets. In cotransfection assays, Skp2NF bound cyclin A while Skp2LRR did not (FIG. 1A). We then determined that the N terminal 100 residues fused with GFP (Skp2N-GFP) were sufficient for cyclin A binding, indicating that the F-box is not required (lanes 7 and 8). We went on to use smaller deletions to map the amino acid residues necessary for binding cyclin A to between residues 40 and 60 in the context of full C-terminal sequences (FIGS. 1B and C).

A commonly used physical relationship between cyclins and non-Cdk proteins is mediated between the RxL motif in the interacting proteins (Adams et al., 1996; Zhu et al., 1995) and the hydrophobic patch (HP) on cyclins (the RxL-HP interaction) (Russo et al., 1996; Schulman et al., 1998). Interestingly, sequences between 40 and 60 of Skp2 do not contain a recognizable RxL motif (FIG. 1D). This sequence however is nearly completely conserved from human Skp2 to mouse and chicken Skp2 orthologs. When the alignment is extended to fly Skp2, four conserved residues can be identified. Mutation of these four conserved residues to alanine (the Skp2AAAA mutant) abolished the ability of the full length Skp2 to bind cyclin A (FIG. 1E). These results demonstrate that Skp2 uses a novel, non-RxL cyclin A binding domain to interact with cyclin A.

Figure 2:
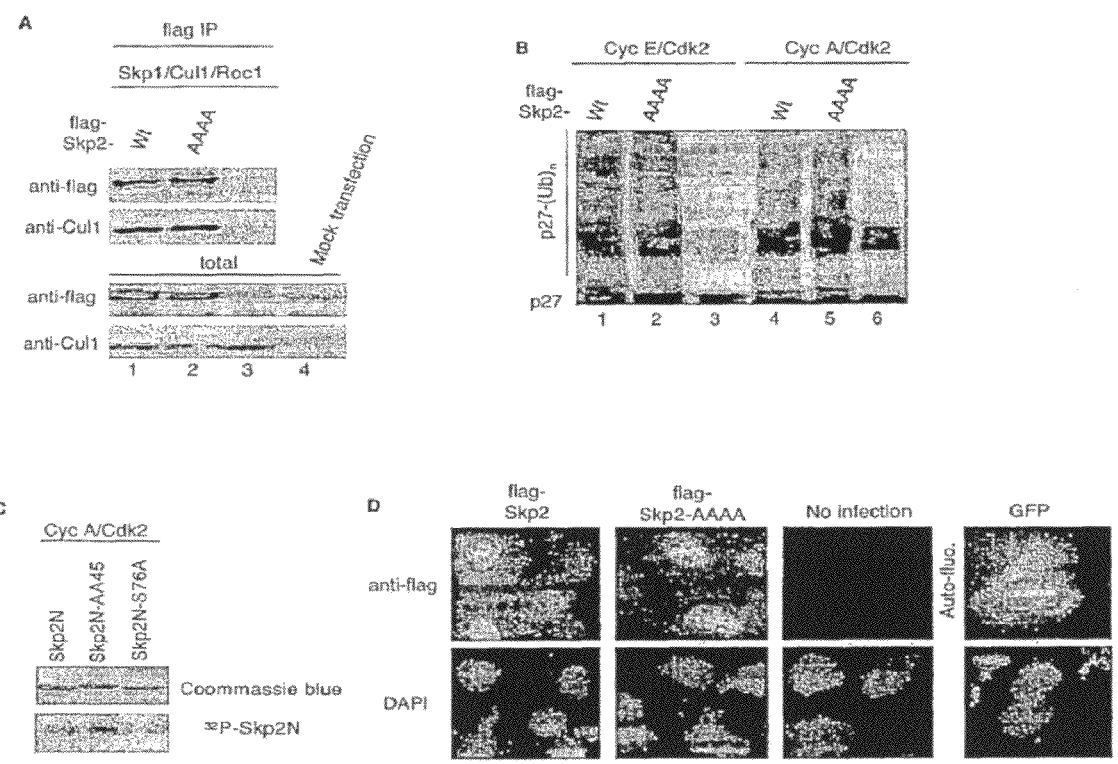
FIG. 2 is photographs of blots and fluorescent micrographs showing that the Skp2-cyclin A interaction is separable from other known activities of Skp2. Panel A shows an IP-Western assay with transfected 293T cell extracts as in FIGS. 1A and B, except expression vectors for SCF$^{Skp2}$Roc1 subunits were used. Skp2 was omitted in transfection for lane 3. Cells in lane 4 were mock-transfected. Panel B shows an in vitro p27 ubiquitylation assay using the immuno-purified complexes shown in panel A. Purified p27 was first phosphorylated by either purified cyclin E/Cdk2 or cyclin A/Cdk2 as indicated. In panel C, various purified GST fusion proteins, as indicated, were incubated in kinase reactions with purified cyclin A/Cdk2. Coomassie Blue stain and autoradiograph of the same gel are shown. In panel D, U2OS cells were infected with lentiviruses expressing GFP, flag tagged Skp2, or flag tagged Skp2AAAA. Expression and cellular localization of Skp2 was revealed by indirect immunofluorescence staining.

Skp2-cyclin A interaction is separable from other known biochemical properties of Skp2. With the ability to disrupt Skp2-cyclin A interaction with point mutations in the Skp2 N-terminus, we determined the role of this interaction in other known biochemical properties of Skp2 by comparing Skp2 and Skp2AAAA. Since the cyclin A binding domain is located N-terminal to the F-box and an N-terminally truncated Skp2 (Skp2ΔN) could form complexes with Skp1-Cul1-Roc1 (Schulman et al., 2000; Zheng et al., 2002), it was predicted that Skp2AAAA should retain the ability to form the $SCF^{Skp2}$Roc1 complex. This prediction was tested by co-expressing the four components of $SCF^{Skp2}$Roc1 complex into 293T cells and immunoprecipitating Skp2 (or Skp2AAAA) via a flag tag on Skp2. The results show that the Skp2AAAA formed $SCF^{Skp2AAAA}$Roc1 complex similarly as Skp2 (FIG. 2A).

Whether the $SCF^{Skp2AAAA}$Roc1 complex is active as an ubiquitin ligase for p27 was next determined. Immuno-purified $SCF^{Skp2}$Roc1 and $SCF^{Skp2AAAA}$Roc1 complexes, supplemented with E1 and E2, were incubated with purified p27 that had been first phosphorylated by cyclin E/Cdk2 or cyclin A/Cdk2. Results shown in FIG. 2B demonstrate that Skp2AAAA retained the ability to ubiquity late p27. No p27 ubiquitylation was observed when p27 was not first phosphorylated by cyclin E/Cdk2 or cyclin A/Cdk2 (data not shown).

Ser76 in the Skp2 N terminus can be phosphorylated by cyclin A/Cdk2 (Yam et al., 1999). Whether the Skp2-cyclin A interaction serves a substrate recruitment function and therefore is required for this phosphorylation was next determined. Results in FIG. 2C show that disruption of the interaction between cyclin A and the Skp2 N-terminus (Skp2N) by point mutations (see also FIG. 3C) did not affect the phosphorylation of Ser76 by cyclin A/Cdk2. Skp2 is a nuclear protein (Lisztwan et al., 1998). Whether Skp2-cyclin A interaction is required for its nuclear localization was determined. As shown in FIG. 2D, both Skp2 and Skp2AAAA are localized in the nucleus when expressed in U2OS cells. Based on these results, it is concluded that Skp2-cyclin A interaction is separable from these known properties of Skp2.

Skp2 binds cyclin A as efficiently as p27. The effects of Skp2-cyclin A interaction on cyclin A/Cdk2 was next determined. p27 is the best-understood RxL protein that bind cyclin A/Cdk2 with high efficiency as a kinase inhibitor. As an approach to understanding the effects of Skp2 on cyclin A/Cdk2, the Skp2-cyclin A/Cdk2 interaction was compared with the p27-cyclin A/Cdk2 interaction.

Figure 3:
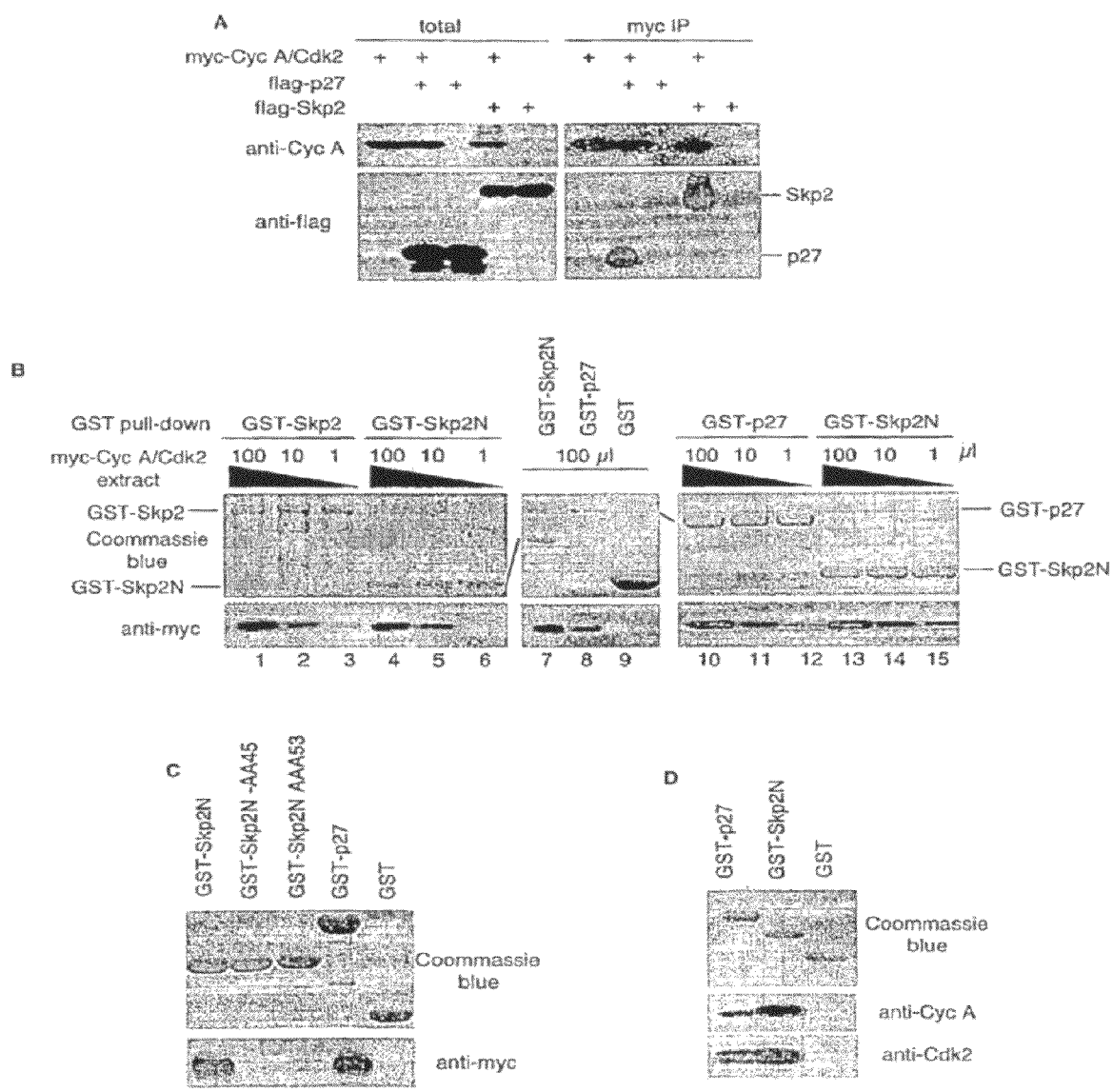
FIG. 3 shows experimental results of comparisons of binding efficiencies of the Skp2-cyclin A and p27-cyclin A interactions. Panel A shows an IP-Western assay of transfected 293T cell extracts as indicated. Panel B shows GST pull-down assays with GST, GST-p27, GST-Skp2, or GST-Skp2N and 293T cell extracts transfected with myc-cyclin A and Cdk2. Panel C shows GST pull-down assays as in panel B, except two GST-Skp2N mutants were included. Panel D shows a GST pull-down assay with the indicated GST-fusion proteins and baculovirally produced and purified GST-cyclin A/Cdk2 complex after GST cleavage.

The binding efficiencies of Skp2-cyclin A/Cdk2 and p27-cyclin A/Cdk2 were first compared. Flag-tagged Skp2 and p27 was used so that the amounts of these two proteins can be compared with anti-flag antibody on Western blots. When expressed at similar levels in transfected 293T cells (FIG. 3A, "total" gels), similar amounts of flag-p27 and flag-Skp2 were co-immunoprecipitated with the cotransfected cyclin A (FIG. 3A, "myc IP" gels). GST pull-down assays were next used to determine the binding efficiencies in vitro. We first showed that the Skp2 N-terminus (Skp2N) can bind cyclin A as efficiently as the full-length Skp2 by titrating down the input amounts of cyclin A/Cdk2 (FIG. 3B, lanes 1 to 6). When the binding efficiencies of Skp2N and p27 were compared in the titration experiments, binding efficiencies were again found to be similar (FIG. 3B, lanes 7-15). FIG. 3C demonstrates that point mutations of the conserved residues in the cyclin A binding sequence (40-60) abolishes cyclin A binding of Skp2N. In that experiment, mutations of two conserved residues (either $AA_{45}$ or $AAA_{53}$) efficiently abolished cyclin A binding. Finally, purified Skp2N and purified p27 were able to bind purified cyclin A/Cdk2 (FIG. 3D), indicating that the Skp2-cyclin A interaction is also direct as the p27-cyclin A/Cdk2 interaction.

Figure 4:
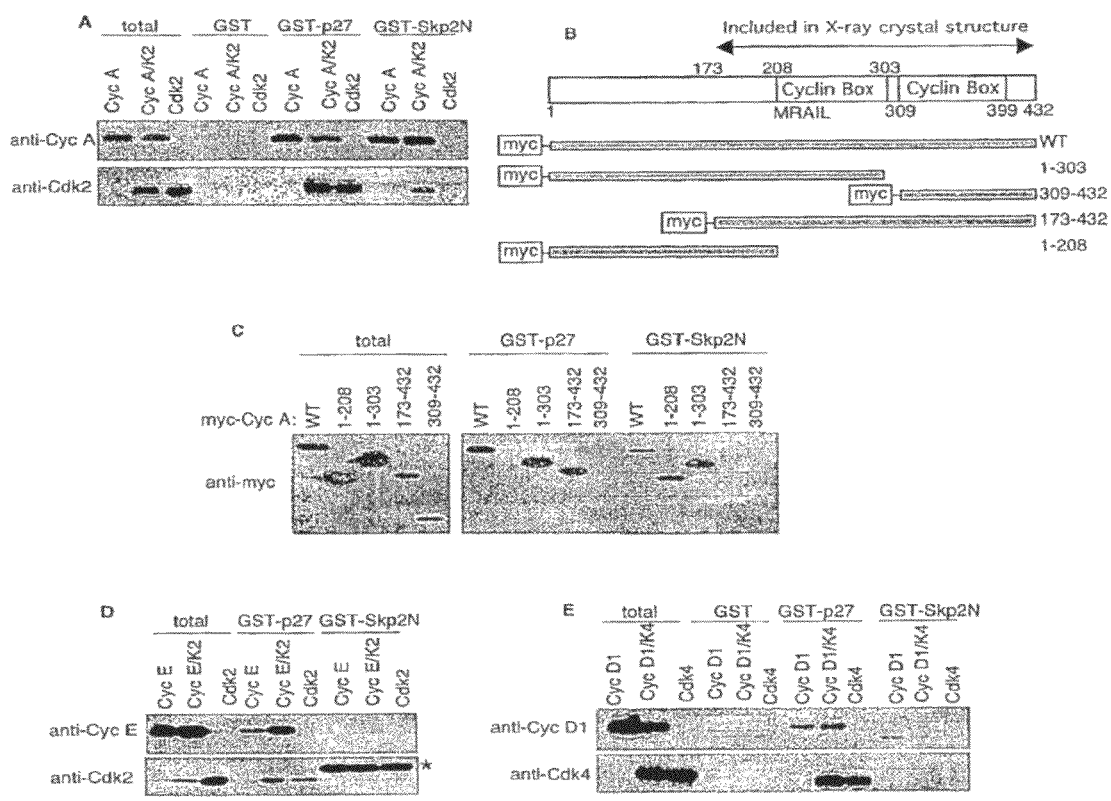
FIG. 4 shows experimental results establishing that Skp2 does not interact with Cdk2 alone and interacts with the N-terminus of cyclin A. Panel A shows a GST pull-down assay with indicated GST fusion proteins and 293T cell extracts transfected with the indicated expression vectors. Panel B shows a schematic drawing of the cyclin A domain structure and various mutants used in the experiments depicted in Panel C below. Panel C shows GST pull-down assays as in panel A, with indicated GST fusion proteins and cell extracts transfected with various cyclin A mutants. Panels D and E show GST pull-down assays as in panel A except with cyclin E/Cdk2 or cyclin D1/Cdk4 transfected cell extracts. The star indicates background bands.

Skp2 and p27 bind to different sequences on cyclin A. Results in FIG. 1 demonstrate that Skp2 uses a novel non-RxL motif to interact with cyclin A. Whether the Skp2-cyclin A/Cdk2 interaction and the p27-cyclin A/Cdk2 interaction also differ on the side of cyclin A/Cdk2 was next investigated. An important feature for the p27-cyclin A/Cdk2 interaction is that, in addition to the RxL-HP interaction, p27 also has an extended interaction with the N-terminal lobe of Cdk2, providing a structural basis for its inhibitory effects on cyclin A/Cdk2 kinase (Russo et al., 1996). To compare this aspect of p27 with Skp2, cyclin A and Cdk2 were expressed separately in 293T cells, and the binding behavior of GST-p27 and GST-Skp2N in these transfected extracts was determined. As shown in FIG. 4A, GST-p27 binds the cyclin A/Cdk2 complex as well as cyclin A or Cdk2 in singly transfected extracts. In the same conditions, GST-Skp2N binds cyclin A/Cdk2 and cyclin A alone but does not bind Cdk2 alone. The amount of Cdk2 was also less in the GST-Skp2N-cyclin A/Cdk2 pull-down than in the GST-p27-cyclin A/Cdk2 pull-down, which is consistent with p27 but not Skp2N, which is also able to bind free Cdk2.

Localization of Skp2 interaction sequences in cyclin A was next determined and compared with p27. Cyclin A contains two conserved cyclin-box sequences that form two cyclin-folds in the cyclin A/Cdk2 crystal structure (Jeffrey et al., 1995), which does not include the N-terminal 172 amino acid residues (FIG. 4B). The hydrophobic patch (HP) that mediates interaction with the RxL motif of p27 is composed of residues $_{210}$MRAILVDW in the a1 helix of the N-terminal cyclin fold (Russo et al., 1996). Based on this information, cyclin A mutants were designed to map and compare Skp2 and p27 binding sequences, as shown in FIGS. 4B and C. Cyclin A sequences 1-303 (consisting of the N-terminal cyclin-fold and the N-terminus) bound to p27 and Skp2N to a similar extent as the full-length cyclin A (compare the relative amounts in total and pull-down gels), while the C-terminal cyclin-fold and the C-terminus (the 309-432 fragment) did not bind p27 or Skp2N. Cyclin A with an N-terminal truncation to residue 173 (which was previously used for crystal structure analysis) bound to p27 to similar extent as full-length cyclin A but barely detectably to Skp2N. This result is in agreement with the determination of HP to be the p27 binding site by crystal structure studies and indicates that a distinct site upstream of residue 173 provide major binding affinity for Skp2N. Consistent with this notion, cyclin A fragment 1-208 can bind to Skp2N but not p27. Identification of the cyclin A N-terminus as the major binding site for Skp2N may provide a structural basis for the cyclin specificity of the Skp2-cyclin A interaction since, unlike the cyclin-box sequences, cyclin A N-terminal sequences are not conserved in other cyclins. Indeed, as shown in FIGS. 4D and E, Skp2N did not interact with cyclin E/Cdk2 or cyclin D1/Cdk4 while p27 showed stable binding to these cyclins.

Figure 5:
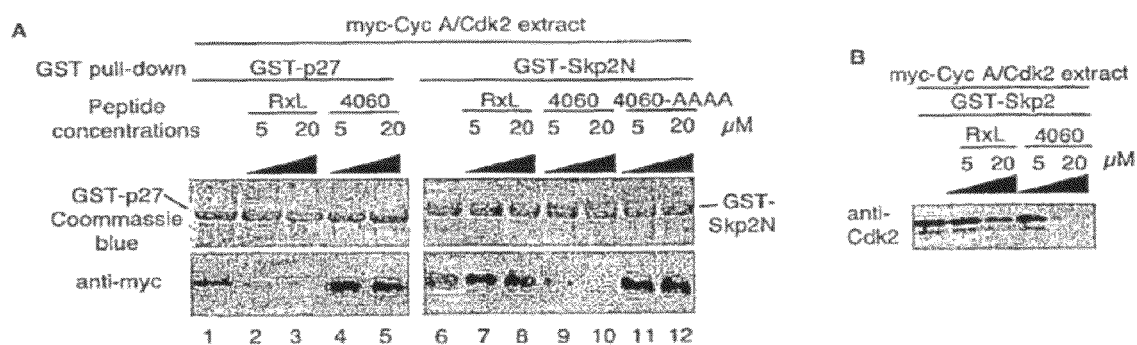
FIG. 5 shows experimental results establishing that the Skp2-cyclin A interaction and the p27-cyclin A interaction are blocked by distinct peptides. Panel A shows GST pull-down assays with indicated GST fusion proteins and myc-cyclin A/Cdk2 transfected 293T cell extracts in the absence and presence of various indicated peptides at indicated concentrations. Panel B shows the same as in panel A except GST-Skp2 was used.

Skp2-cyclin A interaction and p27-cyclin A interaction can be blocked by distinct peptides. An important aspect of the RxL-1-IP interaction is that it can be blocked by a short RxL peptide (Adams et al., 1996). If the Skp2-cyclin A/Cdk2 interaction and the p27-cyclin A/Cdk2 interaction are mediated by different sequences on both sides of the interaction, as shown above, it can be predicted that the RxL peptide should not block Skp2-cyclin A interaction. Experimental results also show that an eighteen-residue peptide replica derived from Skp2 sequences between 40 and 60 (called the 4060 peptide) can block the Skp2-cyclin A interaction but not the p27-cyclin A interaction (FIG. 5A, lanes 9, 10 and 4, 5). Mutations of the four conserved residues to alanine (the 4060AAAA peptide) abolished the blocking activity of the 4060 peptide (lanes 11, 12). The RxL peptide has the opposite effects (blocking the p27-cyclin A interaction but not the Skp2N-cyclin A interaction) (lanes 2, 3 and 6, 7). Peptide concentrations required for their respective blocking activities were similar for RxL and 4060 peptides. The 4060 peptide, but not the RxL peptide, also blocked binding between full-length GST-Skp2 and cyclin A/Cdk2 (FIG. 5B). These results provide strong evidence that Skp2 40-60 sequence contains a novel cyclin A interacting domain and Skp2-cyclin A interaction is distinct from the RxL-HP interaction.

Figure 6:
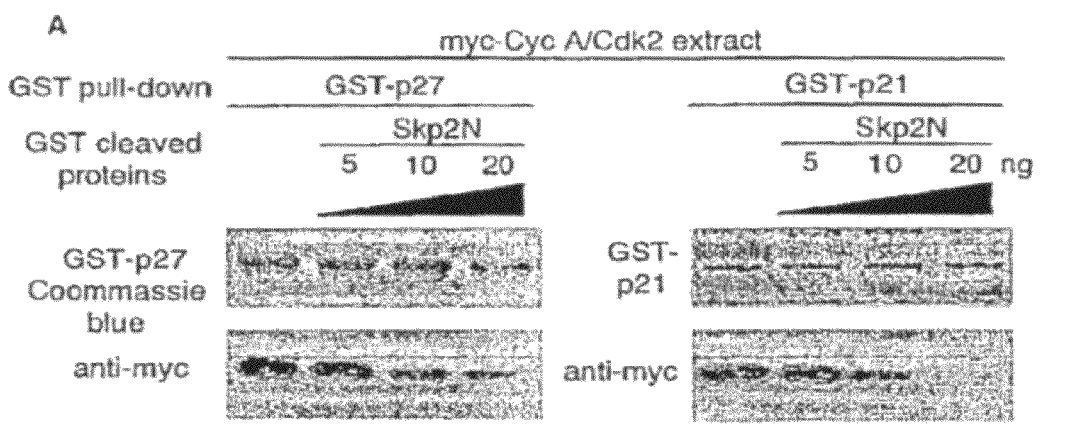
FIG. 6 shows experimental results establishing that Skp2 competes with p27/p21, but not E2F1, for binding to cyclin A. Panel A shows GST pull-down assays with GST-p27 and GST-p21 and myc-cyclin A/Cdk2 transfected 293T cell extracts. Increasing amounts of eluted and GST cleaved Skp2N were added as indicated. In panel B, U2OS cells were treated with 180 nM actinomycin D for 20 hours. Cell extracts were then used for IP-Western blotting as indicated. Panel C shows a GST pull-down assay as in panel A except GST-E2F1 was used.
Figure 6:
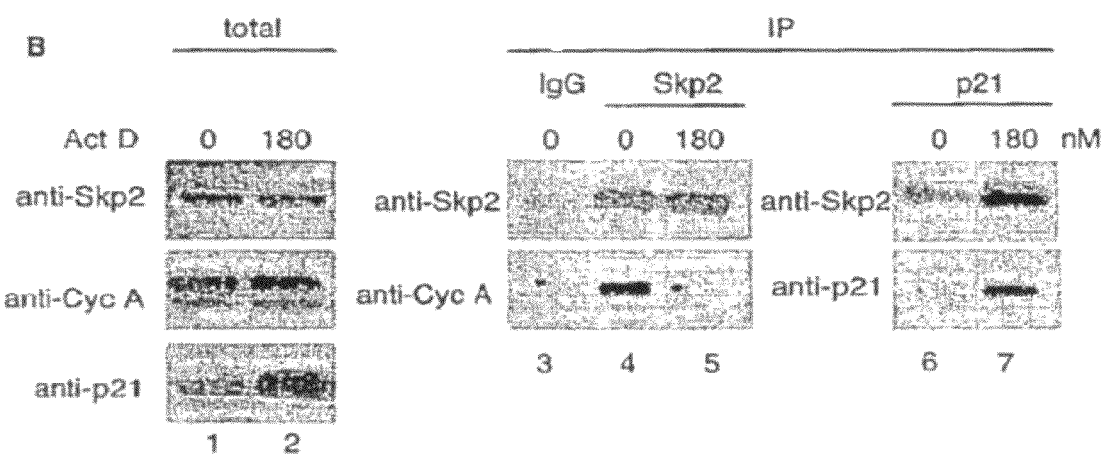
Figure 6:
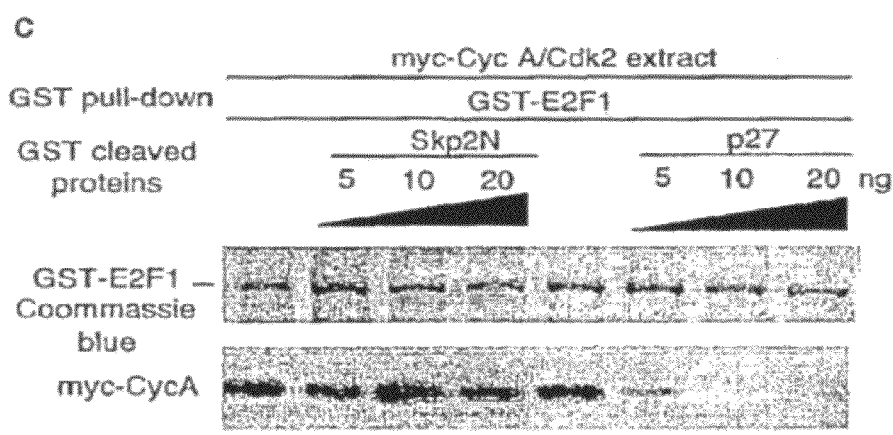

Skp2 competes with p27/p21, but not E2F1, for binding to cyclin A. Whether the apparently distinct Skp2-cyclin A interaction and p27-cyclin A interaction are competitive against each other was next evaluated. As shown in FIG. 6A left, by including progressively higher concentrations of Skp2N in a binding reaction with fixed amounts of GST-p27 and cyclin A/Cdk2, p27 binding to cyclin A was progressively diminished. Skp2N also competed with GST-p21 for binding to cyclin A/Cdk2 (FIG. 6A right). Whether the competition between Skp2 and p27/p21 for cyclin A binding could be observed in vivo with endogenous proteins under physiological conditions was next determined. Since abundant amounts of cyclin A are already bound by Skp2 and very little is bound by p27 or p21 in various cell lines (unpublished results), this issue was addressed from the other direction of competition by testing whether p27/p21 could compete Skp2 away from cyclin A. For this purpose, we treated U2OS cells with actinomycin D to activate p53, which led to a significant increase in p21 protein levels. As shown in FIG. 6B, the increase in p21 levels after actinomycin D treatment in the assay conditions did not change protein levels of Skp2 and cyclin A (lanes 1 and 2) but decreased the Skp2-cyclin A interaction to background levels (lanes 4 and 5) with increased binding of cyclin A to p21 (lanes 6 and 7).

Whether Skp2 competes with another RxL protein, E2F1, for cyclin A binding (Krek et al., 1994) was next determined. E2F1 differs from p21/p27 as a cyclin A binding protein in that it does not inhibit cyclin A/Cdk2 kinase activity and is mainly a phosphorylation substrate. As shown in FIG. 6C, Skp2N did not affect E2F1-cyclin A binding while p27 efficiently blocked it in the same experiment as expected. Thus, Skp2 binding to cyclin A does not block interaction of cyclin A with all RxL proteins, which is consistent with the fact that, unlike p27, Skp2 does not use the RxL-HP mechanism to interact with cyclin A. These binding characteristics apparently provide a molecular explanation for the regulatory effects of Skp2 on cyclin A/Cdk2 kinase activity described below.

The Skp2-cyclin A interaction directly protects cyclin A/Cdk2 from inhibition by p27. The effects of the Skp2-cyclin A interaction on cyclin A/Cdk2 kinase activity has remained unclear and controversial. In the original report, Beach and coworkers showed that the Skp2-cyclin A/Cdk2 interaction did not inhibit nor stimulate cyclin A/Cdk2 kinase activity (Zhang et al., 1995). To the contrary, Poon and coworkers provided evidence that Skp2 could inhibit cyclin A/Cdk2 kinase activity (Yam et al., 1999). We reasoned that a better way to determine the effects of Skp2 on cyclin A/Cdk2 kinase activity is to compare Skp2 with a well-established CKI like p27 and relate amounts and ratios of relevant proteins used in vitro to the respective amounts and ratios of the same proteins in cells. We also used purified proteins in soluble reactions to measure kinase activity under equilibrium conditions to avoid complications associated with immunoprecipitation of the kinases.

Figure 7:
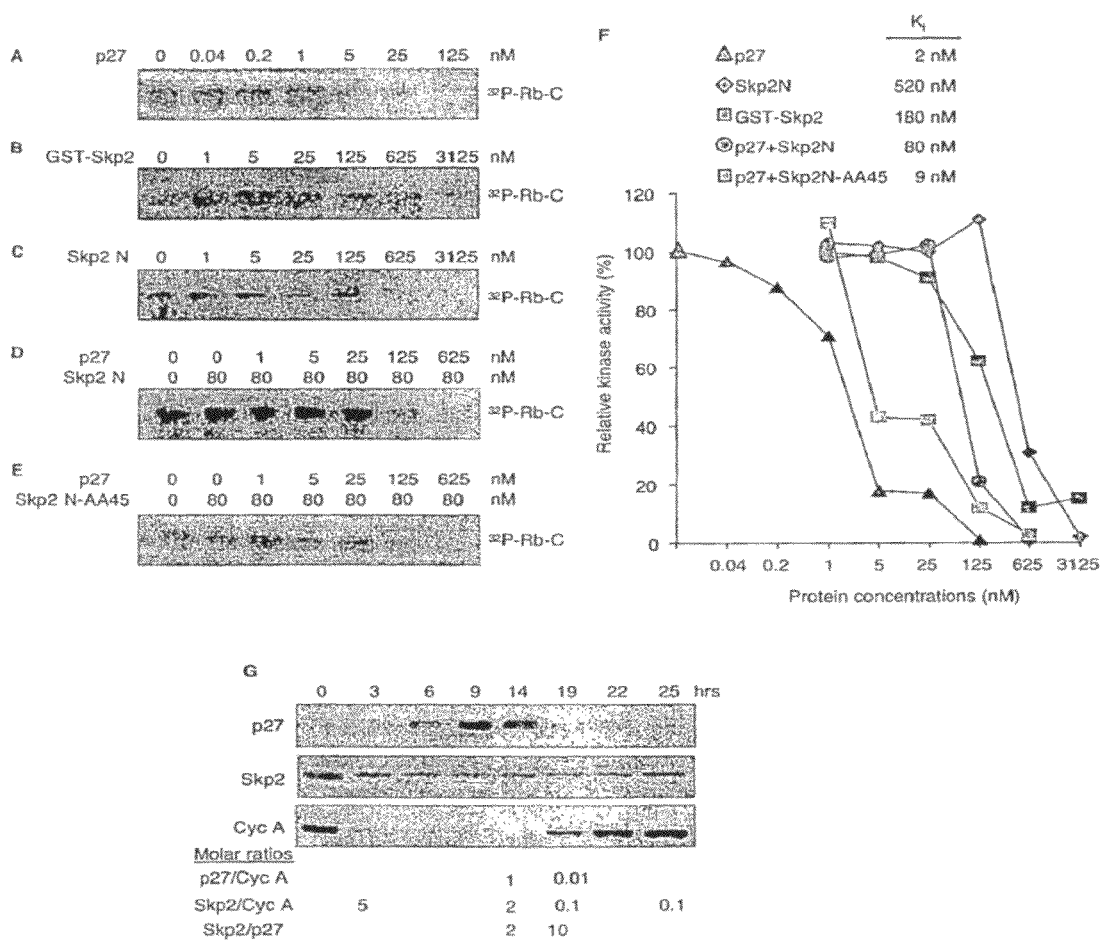
FIG. 7 shows experimental results showing the regulation of cyclin A/Cdk2 kinase activity by Skp2. Panels A-E shows a kinase reaction using purified cyclin A/Cdk2 at ~3 nM. Increasing concentrations of purified p27, GST-Skp2, Skp2N, and Skp2N-AA45 were included in the kinase reaction as indicated. In panel F, the phosphorylation of Rb-C was quantified and plotted to determine the Ki of various proteins. In panel G, HeLa cells were arrested in mitotic phase with nocodazole treatment and released into fresh media at time 0. Fractions of cells were harvested at the indicated time-points and cellular protein levels of p27, Skp2, and cyclin A determined with Western blotting.

For kinase reactions, insect cell-produced and purified GST-cyclin A/Cdk2 was used at a concentration of ~3 nM, which was the lowest concentration that yielded readily detectable phosphorylation of GST-Rb-C here. Purified p27, GST-Skp2, and Skp2N were titrated into the kinase reaction over a wide range of concentrations (FIGS. 7A, B, and C). Phosphorylation of Rb-C was measured and plotted, and the Ki of these various proteins were determined by non-linear least squares analysis (FIG. 7F). Results show that p27 inhibited cyclin A/Cdk2 kinase activity with a Ki of ~2 nM. In the same assay conditions, GST-Skp2 and Skp2N could also inhibit the kinase activity although their Ki of ~180 nM and ~520 nM, respectively, are significantly higher than p27's Ki. This finding suggests that previous discrepant results on Skp2's effects on cyclin A/Cdk2 kinase activity could be due to different amounts of Skp2 used in the kinase assays.

Whether the observed inhibitory effects of Skp2 has physiological relevance was next determined by measuring amounts and ratios of relevant proteins in cells and comparing them with ratios used in kinase assays. Skp2 forms abundant complexes with cyclin A in tumor cells due to its frequent overexpression. HeLa cells were used, which contain higher levels of Skp2 compared with a number of commonly used cell lines (data not shown), to determine whether the Skp2:cyclin A ratios that resulted in kinase inhibition in kinase assays could be reached in cells. Since Skp2, p27, and cyclin A levels oscillate in the cell cycle, their levels were determined in synchronized cell populations obtained at various time points after release from mitotic arrest (FIG. 7G). The quantities of p27, Skp2, and cyclin A were quantified in HeLa cells at various cell cycle stages by comparing them with known amounts of purified Skp2N, p27, and cyclin A in the same Western blots (see Materials and methods). The molar ratios of p27/cyclin A and Skp2/cyclin A was then determined at representative time points in the cell cycle. As shown in FIG. 7G, the p27/cyclin A molar ratio was ~1.0 at 14 hours when cyclin A was starting to accumulate and ~0.01 at 19 hours when cyclin A has reached significant levels while p27 levels decreased. Since the Ki of p27 is ~2 nM in the kinase reaction containing 3 nM of cyclin A, these molar ratios suggest that p27 could function as an effective CKI at 14 hours but not at 19 hours. When the same analysis was applied to Skp2, it was revealed that the highest Skp2/cyclin A molar ratio found at 3 hours is about ~5, which is well below the molar ratio at the Ki of Skp2 (~180 nM of Skp2 over 3 nM of cyclin A/Cdk2). Although it is formally possible that certain factors could affect or modify the activity of Skp2 in vivo, the large gap between Skp2/Cyclin A molar ratios in vivo and that required to reach Ki in vitro suggests that Skp2 is unlikely to function as an inhibitor of cyclin A/Cdk2 kinase activity.

Since Skp2 competes with p27 for binding to cyclin A and Skp2's Ki is about 100-fold higher than p27's Ki, it can be reasoned that, at concentrations well below its Ki, Skp2 might be able to protect cyclin A/Cdk2 from inhibition by p27. To test this hypothesis, the same cyclin A/Cdk2 kinase assay was carried out to determine the inhibitory activity of p27 in the presence of 80 nM of Skp2N. The results in FIGS. 7D and E show that inclusion of Skp2N, but not Skp2N-AA45, increased the Ki of p27 from ±2 nM to ±80 nM, revealing a protective effect of Skp2. Protein molar ratio analysis suggests that this protective effect could be effective at 14 hours, when cyclin A levels start to rise and Skp2 is present in about 2-fold excess over p27 (FIG. 7G).

Figure 8:
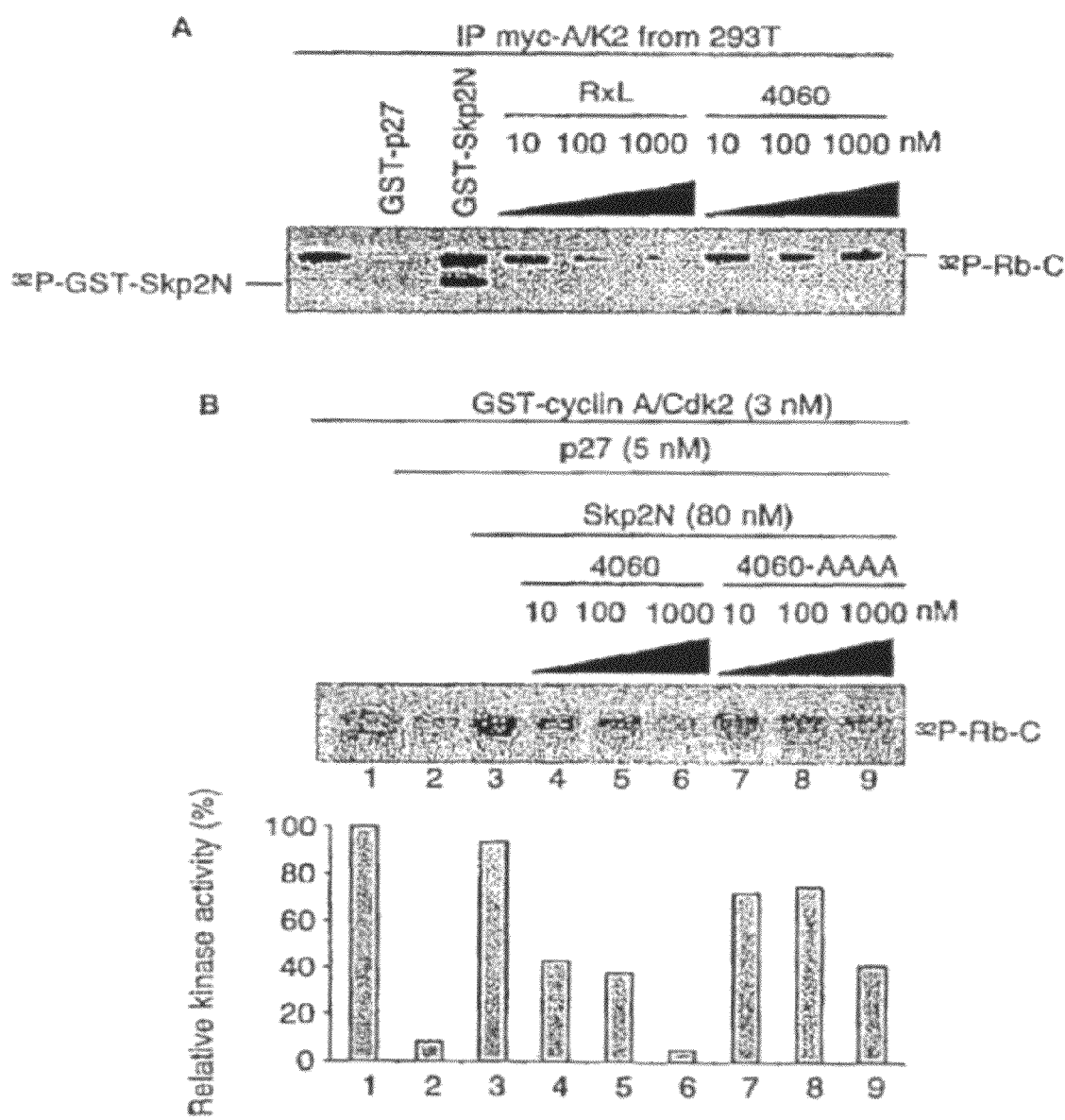
FIG. 8 shows experimental results establishing that the 4060 peptide can prevent Skp2 from protecting cyclin A from inhibition by p27. In panel A, an IP-kinase assay was performed with myc-cyclin A/Cdk2 transfected 293T cell extract in the presence of increasing amounts of RxL or 4060 peptides. Phosphorylation of GST-Skp2N is visible in this gel. Panel B shows an in vitro kinase assay with purified proteins as in FIG. 7A. As indicated, increasing amounts of the 4060 or 4060AAAA peptides were included in the reactions. Phosphorylation of Rb-C was quantified and plotted as shown.

Since the 4060 peptide can disrupt Skp2-cyclin A binding but not p27-cyclin A binding most likely due to its small size (FIG. 5A), it should prevent Skp2 from protecting cyclin A/Cdk2 from inhibition by p27. The effect of the 4060 peptide itself on cyclin A/Cdk2 kinase activity was first determined. As shown in FIG. 8A, while the RxL peptide inhibited the kinase activity of cyclin A/Cdk2 towards Rb-C as expected (Adams et al., 1996), the 4060 peptide did not. This result is again consistent with data presented in FIGS. 1, 4, and 5 that Skp2 40-60 sequences represent a non-RxL cyclin A binding domain.

It was then determined whether the 4060 peptide could prevent Skp2N from protecting cyclin A/Cdk2 from inhibition by p27. As shown in FIG. 8B, the kinase activity of cyclin A/Cdk2 is efficiently inhibited by 5 nM of p27 (lane 2). When 80 nM of Skp2N was included, 5 nM of p27 lost its ability to inhibit the kinase activity (lane 3). When increasing amounts of 4060 peptide were also included in the reaction, p27 gradually regained its inhibitory effects (lanes 4 to 6). The 4060AAAA peptide did not have significant effects. These results provide further support for a protective role of the Skp2-cyclin A interaction in regulation of cyclin A/Cdk2 kinase activity. These findings indicate that the Skp2-cyclin A interaction is also a potential target to inhibit cyclin A kinase activity in tumor cells, particularly those overexpressing Skp2.

Figure 9:
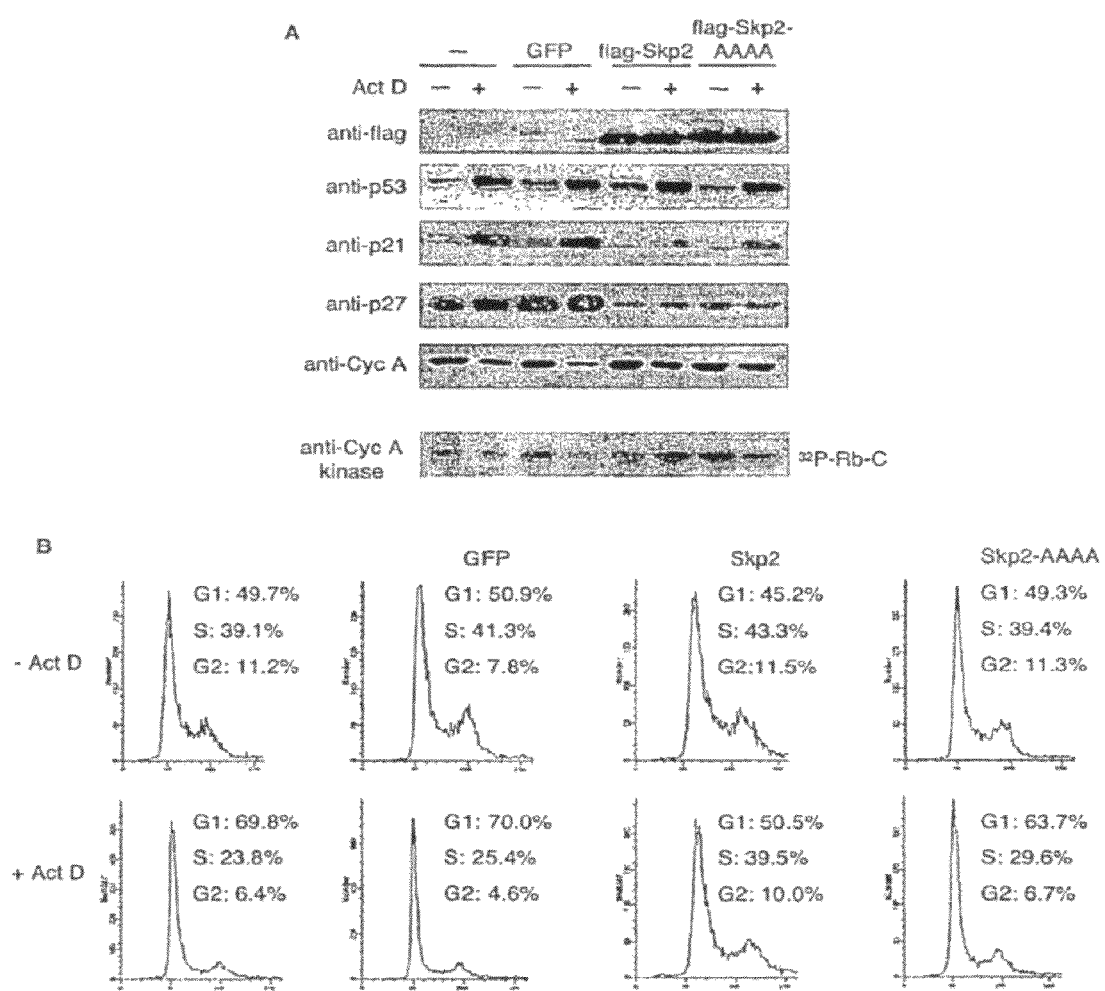
FIG. 9 shows experimental results establishing that the AAAA mutation to the 4060 peptide does not affect Skp2-mediated degradation of p27 and p21, but significantly compromises Skp2's ability to counter a p53-p21 mediated G1 cell cycle arrest. In panel A, U2OS cells were infected with various lentiviruses as indicated and treated with actinomycin D for 20 hours. Total cell extracts were analyzed by Western blotting. In panel B, the same cells were stained with propidium iodide and their DNA profiles were determined by flow cytometry.

The AAAA mutation compromises Skp2's proliferation stimulatory activity without affecting its ability to cause degradation of cellular p27 and p21. Skp2 exhibits proliferation-promoting activities in various assays, which have been attributed to Skp2-mediated p27 ubiquitylation and degradation. With a better understanding of the Skp2-cyclin A interaction and the ability to disrupt this interaction with point mutations that did not affect Skp2's ubiquitylating function, the role of Skp2-cyclin A interaction in the proliferation-stimulating activity of Skp2 was next determined. Similar to the experiment shown in FIG. 6B, U2OS cells were treated with actinomycin D, which led to activation of p53, stimulation of p21 expression, and G1 cell cycle arrest manifested by a 20% increase in G1 phase cells (FIGS. 9A and B). Skp2 was overexpressed in U2OS cells to determine whether Skp2 could counter the G1 cell cycle arrest mediated by this actinomycin D triggered checkpoint.

In untreated cells, overexpression of Skp2 led to a significant reduction of p27 levels (FIG. 9A, anti-p27 western blot) and marked increase in cyclin A associated kinase activity measured with anti-cyclin A immunoprecipitates (bottom panel). Overexpression of Skp2AAAA to similar levels as Skp2 reduced p27 and increased cyclin A-associated kinase activity to similar degrees, consistent with the finding that Skp2AAAA was able to mediate p27 ubiquitylation in vitro (FIG. 2B). Skp2, but not Skp2AAAA, also led to a slight (~4%) increase in S phase populations (FIG. 9B). More significantly, overexpression of Skp2 largely prevented the increase in p21 levels [which is consistent with previous findings that Skp2 can also target p21 for ubiquitylation (Bornstein et al., 2003)], the decrease in cyclin. A associated kinase activity, and the cell cycle arrest after actinomycin D treatment (with only a 5% increase in G1 cell population as compared with a 20% increase in G1 cell populations in uninfected and GFP-infected cells). In comparison, Skp2AAAA was fully competent in reducing p21 protein levels after actinomycin D treatment, but was compromised in its ability to maintain cyclin A-associated kinase activity and to counter the G1 cell cycle arrest after actinomycin D treatment (with a 15% increase in G1 cell population). Activation of p53, as demonstrated by increases in p53 protein levels after actinomycin D treatment was not affected by either Skp2 or Skp2AAAA. These results demonstrate that Skp2-cyclin A interaction has a significant role in Skp2's proliferation-stimulating activity in the context of its overexpression.

Discussion

The Skp2-cyclin A interaction reveals a novel way to physically interact with cyclin A. Cyclin/Cdk as a core kinase complex interacts with other proteins for regulation and substrate recruitment. Interaction between the hydrophobic patch (HP) of a cyclin and an RxL motif of an interacting protein represents a paradigm of this relationship. Skp2 contains a potential RxL motif (the $KxL_{376}$ sequence) and mutation of $KxL_{376}$ to $AAA_{376}$ abolished its interaction with cyclin A, suggesting that Skp2 belongs to the RxL protein family (Lisztwan et al., 1998). Interestingly, the $AAA_{376}$ mutation also abolished Skp2-Skp1 binding (Lisztwan et al., 1998) suggesting that this mutation might have multiple effects. Subsequent X-ray crystal structure studies revealed that Skp2 (with N-terminal truncation of 100 residues) has a rigid structure shaped like a sickle (Schulman et al., 2000). Skp2 F-box sequence and Skp1 together form the handle while the $KxL_{376}$ sequence is buried inside the curved blade. Based on this structural feature, it is likely that the effects induced by the $AAA_{376}$ mutation could be due to more general protein conformational changes.

Results from our current study identify a non-RxL cyclin A binding domain in the Skp2 N-terminus. Skp2 sequences between amino acid residues 40 to 60 are required for cyclin A binding, are highly evolutionarily conserved, and point mutations of the four most conserved residues are sufficient to disrupt the Skp2-cyclin A interaction. Since the Skp2 N-terminal sequences were not included in the solved Skp2 structure, it is not known whether this 40-60 sequence is surface-exposed for protein-protein interaction. Nevertheless, our findings that the 4060 peptide, but not the RxL peptide, can block the Skp2-cyclin A interaction and, conversely, the RxL peptide, but not the 4060 peptide, can block the p27-cyclin A/Cdk2 interaction, provide strong evidence for the presence of a non-RxL cyclin A-interacting sequence between Skp2 residues 40 and 60.

On the cyclin A side, the Skp2-cyclin A interaction also differs from the RxL-HP interaction. When Skp2 and p27 were studied together, the mapping results show that the binding sites on cyclin A for these two proteins are distinct, with the Skp2 binding site located N-terminal to the HP site on the cyclin A N-terminus. At the amino acid sequence level, mapping of the Skp2 interaction site to the N-terminus provides a structural explanation for the cyclin-specificity of the Skp2-cyclin A interaction since the N-terminal sequences of cyclin A are not highly conserved in other cyclins. This finding suggests an interesting possibility that N-termini of various cyclins could be exploited to subject them to specific regulation. In this respect, it will be interesting to understand with further studies the reasons for Skp2 to specifically target cyclin A. A clue may lie in the fact that cyclin A is unique in the cyclin family in that it plays important roles in both G1/S and G2/M phases of the cell cycle.

The RxL-HP interaction was thought to be a general mechanism mediating relationships between cyclins and non-Cdk proteins. Determination that the Skp2-cyclin A interaction represents a novel physical relationship between cyclin A and non-Cdk proteins broadens our view of how cyclins and non-Cdk proteins could interact, which should lead to new knowledge of how cyclins and non-Cdk proteins communicate and regulate each other.

Significance of the Skp2-cyclin A interaction in Skp2-mediated p27 ubiquitylation. In addition to phosphorylating p27 at T187, the cyclin A/Cdk2 complex (or cyclin E/Cdk2 complex) is also required to form trimeric complexes with p27 for its ubiquitylation by Skp2 (Montagnoli et al., 1999). One clue to the nature of this requirement stemmed from the identification of Cks1 as an essential cofactor in p27 ubiquitylation by Skp2 (Ganoth et al., 2001; Spruck et al., 2001). Since Cks1 is a high-affinity Cdk2 binding protein (Bourne et al., 1996), interactions between Cks1 and Cdk2 may facilitate the recruitment of the trimeric cyclin A/Cdk2-p27 complex to Skp2. Structure and mutagenesis studies of Cks1 suggests that Cks1 is a three-faceted protein and it uses its three binding interfaces to separately interact with Skp2, Cdk2, and phosphorylated p27 to organize these proteins into a super-complex (Sitry et al., 2002). In that model, phosphorylated p27 simultaneously interacts with cyclin A/Cdk2 (via the RxL-HP interface), Cks1 (via phosphorylated T187 and Cks1's anion-binding site), and Skp2. The interaction between Skp2 and cyclin A is mediated through Cdk2-Cks1, with Cks1 directly bound near the C-terminus of Skp2 (Wang et al., 2003). The Skp2-N terminus is not involved and no clear distinctions exist between the roles of cyclin A and cyclin E in this super-complex.

X-ray crystal structure studies have provided direct and more detailed evidence for the formation of a cyclin A/Cdk2-Cks1-Skp2-p27 super-complex as proposed above. An N-terminally truncated Skp2 (Skp2ΔN) is able to form a $SCF^{Skp2\Delta N}$Roc1 complex through the F-box (Schulman et al., 2000; Zheng et al., 2002) and a Skp2ΔN-Cks1-p27 complex through the C-terminal blade (Hao et al., 2005). Super-imposing the available cyclin A/Cdk2, Cdk2-Cks1, Skp1-Skp2ΔN-Cks1-p27, and Skp20N-Skp1-Cul1-Roc1 structures demonstrates that a super-complex of Skp1-Skp2ΔN-Cks1-Cdk2/cyclin A-p27 could indeed form on Skp2 (Hao et al., 2005). Skp2ΔN also co-eluted with Skp1, Cul1, Roc1, Cks1, p27, Cdk2, and cyclin A from size-exclusion chromatographic columns, providing experimental evidence for such a eight-subunit complex in the absence of Skp2 N-terminus (Hao et al., 2005).

Interestingly, Koff and coworkers recently reported that bacterially produced Skp20N (which was used for X-ray crystal structure studies) was unable to bind cyclin A and ubiquitylate p27 (Zhu et al., 2004). This result suggests that the eight-subunit complex formed with Skp20N would be functionally inactive in p27 ubiquitylation. A conceivable mechanism for the requirement for the N-terminally bound cyclin A is that, while cyclin A can be tethered onto the Skp2 C-terminus via the Cks1-Cdk2-cyclin A interaction, an additional interaction between cyclin A and the Skp2 N-terminus is needed to strengthen and/or reshape this super-complex for it to be active. The finding that the Skp2 N-terminus and p27 compete for binding to cyclin A/Cdk2 makes this scenario unlikely since when cyclin A/Cdk2 is bound to the Skp2 N-terminus, it will not be able to bind p27 to form the trimeric complex. The results that the Skp2AAAA mutant lost interaction with cyclin A but was able to ubiquitylate p27 provides experimental evidence that an N-terminally bound cyclin A is not required for Skp2 to mediate p27 ubiquitylation. It is possible that other functions in the Skp2 N-terminus may be required for p27 ubiquitylation. Bacterially produced Skp2ΔN may also lack certain important modifications, since Skp2ΔN was able to mediate p27 ubiquitylation when co-expressed in 293T cells with Skp1-Cul1-Roc1 (Ji et al., 2004); and promote degradation of p27 and p21 in HeLa cells (Bashir et al., 2004).

The Skp2-cyclin A interaction represents a new regulatory mechanism of cyclin A/Cdk2 and a new functional mechanism for Skp2's proliferation-stimulating activity. With respect to regulation of cyclin/Cdk by a stably bound protein, the CKI p27 is the best-understood example. In addition to the RxL-HP interface, an N-terminal sequence (residues 85-90) of p27 inserts itself into the catalytic cleft of Cdk2 to block ATP binding (Russo et al., 1996). With this mechanism, the relative concentrations of p27 and cyclin/Cdk will determine the degree of kinase inhibition. Skp2-mediated p27 ubiquitylation and degradation can positively regulate cyclin/Cdk2 kinase activity by reducing p27 levels.

This study of the Skp2-cyclin A interaction revealed that the inhibitory effect of p27 on cyclin A/Cdk2 is also regulated by Skp2 independent of p27 ubiquitylation and degradation. Skp2 competes with p27 for binding to cyclin A/Cdk2 but Skp2 itself does not inhibit cyclin A/Cdk2 at physiologically relevant concentrations. This property of Skp2 forms the mechanistic basis for Skp2 to exert a positive effect on cyclin A/Cdk2 whenever p27 is present. The determination that the presence of the Skp2 N-terminus at 80 nM in the kinase reaction shifted the Ki of p27 rightward from 2 nM to 80 nM indicates that this protective effect of Skp2 N-terminus is effective when the molar ratio of Skp2 over p27 is about 1 or larger. The molar ratio of cellular Skp2 over p27 was also determined to be about 2 at 14 hours after HeLa cells were released from mitotic arrest when cyclin A protein levels are starting to rise. While other factors such as cellular localization or compartmentalization can certainly affect the effective concentrations of Skp2 and p27 in vivo, we take these results to indicate that the protective effect of Skp2 is physiologically relevant, at least when Skp2 is overexpressed in tumor cells. These findings therefore add a new mechanism of regulation of cyclin A/Cdk2 kinase activity in that the outcome of regulation of cyclin A/Cdk2 kinase activity by p27 is determined not only by its levels but also by the levels of Skp2. This new mechanism is likely to be applicable to the p27 family member p21 since Skp2 and p21 also compete for cyclin A binding.

By revealing the functional significance of the Skp2-cyclin A interaction, our study also adds a new functional mechanism for Skp2's proliferation-stimulating activity. In an assay that measures the ability of Skp2 to counter cell cycle arrest by p53-p21 mediated cell cycle checkpoint, it was found that point mutations that disrupt Skp2-cyclin A interaction but not p27 ubiquitylation and degradation significantly compromise the ability of Skp2 to counter cell cycle arrest, revealing the importance of the Skp2-cyclin A interaction in Skp2 function in addition to p27 ubiquitylation and degradation in the context of overexpression. The fact that the Skp2 protein is often overexpressed and forms abundant Skp2-cyclin A complexes in various cancer cells indicates that Skp2's direct protective effects on cyclin A may play an important role in natural tumorigenesis as well. In this respect, it is of note that while the inverse correlation of Skp2 and p27 levels have been found in a large number of cancer samples, cancer samples with high Skp2 but no reduction of p27 clearly exist (for prostate cancer as an example, see (Ben-Izhak et al., 2003; Drobnjak et al., 2003; Yang et al., 2002)). In these cancer cells, it is conceivable that certain steps for p27 ubiquitylation and/or degradation may have been disrupted to render Skp2's p27 ubiquitylation activity ineffective, but Skp2's direct protective effects of cyclin A should remain effective and could drive selection for Skp2 overexpression during tumorigenesis. New knowledge of the Skp2-cyclin A interaction should also help reveal new targets for inhibiting proliferation of Skp2-overexpressing tumor cells.

Example 2

Disrupting Skp2-Cyclin A Interaction with a Blocking Peptide Induces Selective Cancer Cell Killing This example is substantially published as Ji et al., 2007.

Example Summary

Skp2 fulfills the definition of an oncoprotein with its frequent overexpression in cancer cells and oncogenic activity in various laboratory assays and therefore is a potential cancer therapy target. The best-known function of Skp2 is that of an F-box protein of the $SCF^{Skp2}$-Roc1 E3 ubiquitin ligase targeting the cyclin-dependent kinase inhibitor $p27^{Kip1}$. Knockdown of Skp2 generally leads to accumulation of p27, but its effects on cancer cells are less certain. Another function of Skp2 is its stable interaction with cyclin A, which directly protects cyclin A from inhibition by p27 in in vitro kinase assays. Here, it is reported that an eighteen-residue blocking peptide of Skp2-cyclin A interaction can indirectly inhibit cyclin A/Cdk2 kinase activity dependent on the presence of p27 in in vitro kinase assays. Trans-membrane delivery of this blocking peptide can induce cell death in a panel of four cancer cell lines in which Skp2 knockdown only have mild inhibitory effects. This Skp2-cyclin A interaction blocking peptide can synergize with a previously identified E2F1-derived LDL peptide, which blocks its access to cyclin A, in killing cancer cells. $IC_{50}$ of the Skp2-cyclin A blocking peptide correlated with abundance of Skp2, its intended target, in cancer cells. These results suggest that Skp2-cyclin A interaction plays an important role in cancer cell survival and is an attractive target for cancer drug discovery.

Introduction

Skp2 was identified and cloned as a cyclin A binding protein (Zhang et al., 1995) and an F-box protein (Bai et al., 1996). It is now well established that Skp2 is the substrate recruiting subunit of the $SCF^{Skp2}$-Roc1 E3 ubiquitin ligase targeting p27 for ubiquitylation (Cardozo and Pagano, 2004). Since p27 is a negative regulator of cell proliferation (Sherr and Roberts, 1999), the p27 ubiquitylation activity of Skp2 and its overexpression in cancer cells suggested that it might be an oncoprotein. Indeed, Skp2 meets the criteria for an oncoprotein with frequent overexpression in a wide range of cancer specimens, and oncogenic activity in various experimental assays (Cardozo and Pagano, 2004).

Importantly, in experimental oncogenic studies, oncogenic activities of Skp2 overexpression were not mimicked by inactivation of p27, indicating that Skp2's oncogenic functions involve activities in addition to p27 ubiquitylation and degradation. This contrasts with Skp2's role in mouse development, in which phenotypes of Skp2 knockout can mostly be corrected by p27 knockout (Nakayama et al., 2004; Kossatz et al., 2004). Thus, mechanisms of Skp2 functions in normal physiology and in oncogenesis must be different. This difference may provide an opportunity to develop anti-Skp2 therapeutics for cancer cell-selective therapy.

Molecular details of Skp2's activity in recruiting p27 into the $SCF^{Skp2}$-Cks1-Roc1 complex have been revealed in great details (Hao et al., 2005), which form the basis for inhibitor development for this aspect of Skp2 function (Cardozo and Pagano, 2004). In the meantime, a number of studies have already used gene silencing to determine the effects of targeting Skp2 in cancer cells (Lee and Mccormick, 2005; Kudo et al., 2005; Jiang et al., 2005; Sumimoto et al., 2005). Consistent with Skp2 as a substrate recruiting subunit of the $SCF^{Skp2}$-Roc1 ubiquitin ligase targeting p27, knockdown of Skp2 generally leads to increases in p27 protein levels. However, the biological effects of Skp2 knockdown in cancer cells vary among various degrees of proliferation inhibition, cell death, or lack of effect. These studies provided prove-of-principle that targeting Skp2 could be therapeutic for certain cancers, but raised the need to more carefully determine its potential in this regard. This study was therefore initiated by determining the effects of Skp2 knockdown in four human cancer cell lines with various functional status of p53 and Rb.

Example 1 establishes that the functional significance of the stable Skp2-cyclin A interaction is for Skp2 to directly protect cyclin A/Cdk2 from inhibition by p27. Since this interaction is specific for cyclin A in the cyclin family, specific inhibition of Skp2-cyclin A interaction could create a cellular condition that is distinct from knockdown of Skp2 which leads to inhibition of multiple cyclins together by increased levels of p27. It was therefore determined whether specific inhibition of Skp2-cyclin A interaction by a blocking peptide could lead to inhibition of cyclin A/Cdk2 kinase activity and could have different effects on cancer cells than knockdown of Skp2.

Results

Figure 10:
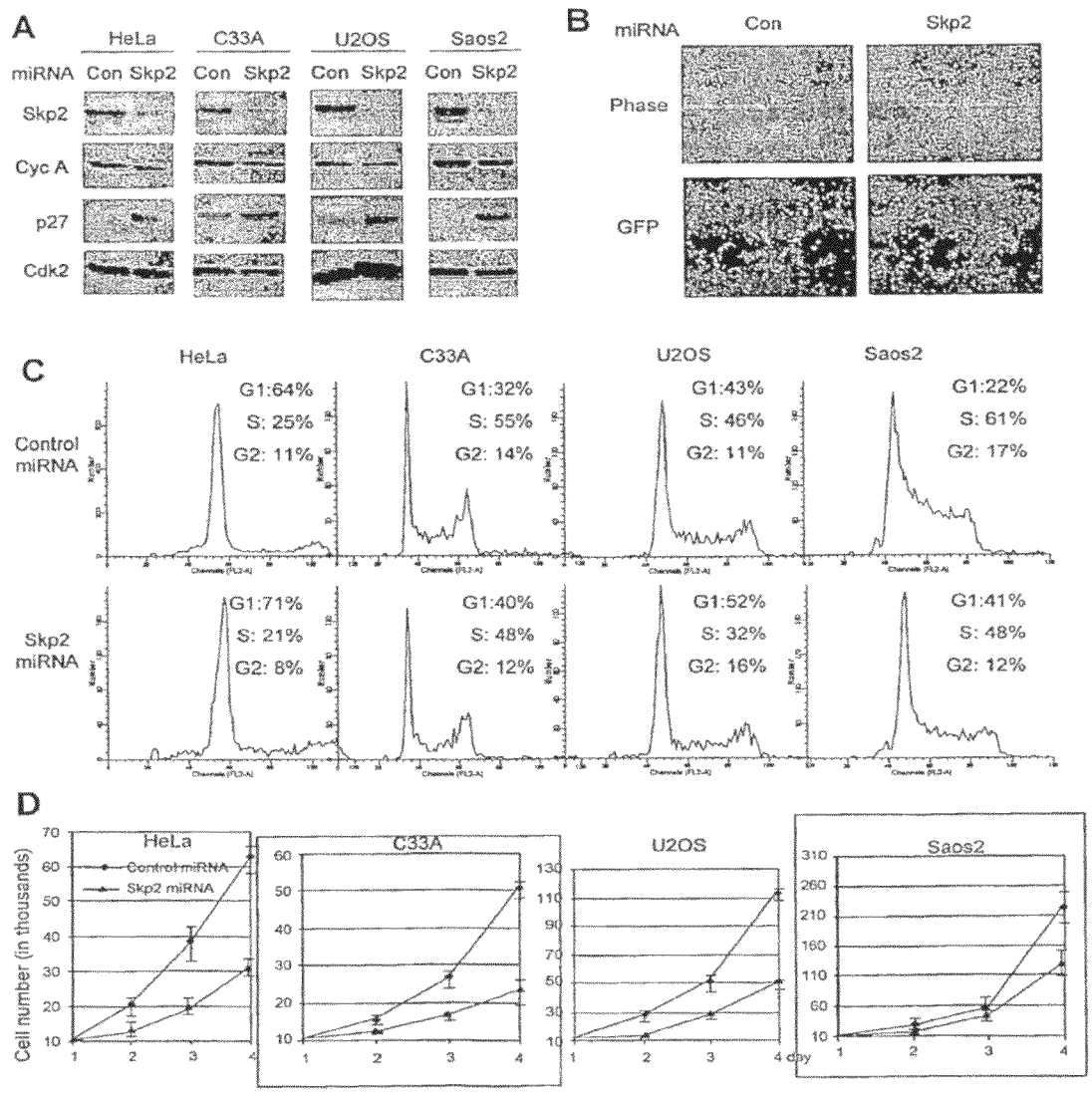
FIG. 10 is photographs of western blots, micrographs and graphs showing Skp2 knockdown in four human cancer cell lines. Panel A shows western blots of indicated cells infected with lentivirus expressing miRNA hairpins targeting Skp2 or an irrelevant mouse sequence as control (Con) for forty-eight hours. Panel B shows phase contrast and GFP fluorescence pictures of U2OS cells infected with the indicated lentiviruses for forty-eight hours. Panel C shows an FACS analysis of the indicated cells forty-eight hours after infection. Panel D shows cell proliferation assays of indicated cancer cells infected with the indicated lentiviruses. Cells in twenty four-wells in triplicate were counted everyday for four days.

Knockdown of Skp2 in a panel of four human cancer cell lines results in mild proliferation inhibition. A recently established multi-microRNA hairpin method was used to achieve effective knockdown of Skp2 in a panel of four human cancer cell lines including cervical carcinoma cell lines HeLa and C33A, and osteosarcoma cell lines U2OS and Saos-2. HeLa cells contain papilloma virus oncoprotein E6 and E7, which disrupt functions of p53 and Rb, respectively, while C33A cells contain a non-functional Rb. Saos-2 cells are defective in p53 and Rb functions due to mutations in both genes, while p53 and Rb functions are intact in U2OS cells. Knockdown hairpins were expressed from a CMV promoter in a single transcript with GFP from a lentivirus vector. An irrelevant hairpin expressed from the same vector was used as control. As shown in FIG. 10A, Skp2 was efficiently knocked down in all four cancer cell lines at forty-eight hours after lentiviral transduction of all the cells in culture as demonstrated by GFP expression (FIG. 10B and data not shown). Knockdown of Skp2 resulted in accumulation of p27 as expected. In comparison, cyclin A and Cdk2 levels did not show significant and consistent change. The slight decreases in cyclin A protein levels after Skp2 knockdown in C33A and Saos-2 cells were not detected reproducibly.

At forty-eight hours after transduction when Skp2 was efficiently knocked down, no visual effects were observed in any of the four cell lines (FIG. 10B and data not shown). Flow cytometry analysis was performed to determine the effects of Skp2 knockdown on cell cycle profile (FIG. 10C). Results showed increases in G1 phase cell populations of about 10-20% with corresponding decreases in S phase populations in these cells with Saos-2 affected most significantly. Consistent with the lack of cell death upon visual examination, no sub-G1 cells were observed in any of the four cell lines after Skp2 knockdown. Their proliferation was then determined during a course of four days as shown in FIG. 10D. A two to three-fold reduction in cell numbers was observed in all four cell lines by day four. These results demonstrate that Skp2 knockdown had a general and mild proliferation inhibition effect in these four cancer cell lines with various status of p53 and Rb. Knockdown of Skp2 with a separate target sequence yielded similar results.

Targeting Skp2-cyclin A interaction with a blocking peptide inhibits cyclin A/Cdk2 kinase activity in the presence of p27. The cyclin A binding aspect of Skp2 function was next evaluated. Identification of an eighteen-residue peptide (the 4060 peptide) that can specifically block Skp2-cyclin A interaction (Example 1) provided a means to study the functional significance of this interaction.

Figure 11:
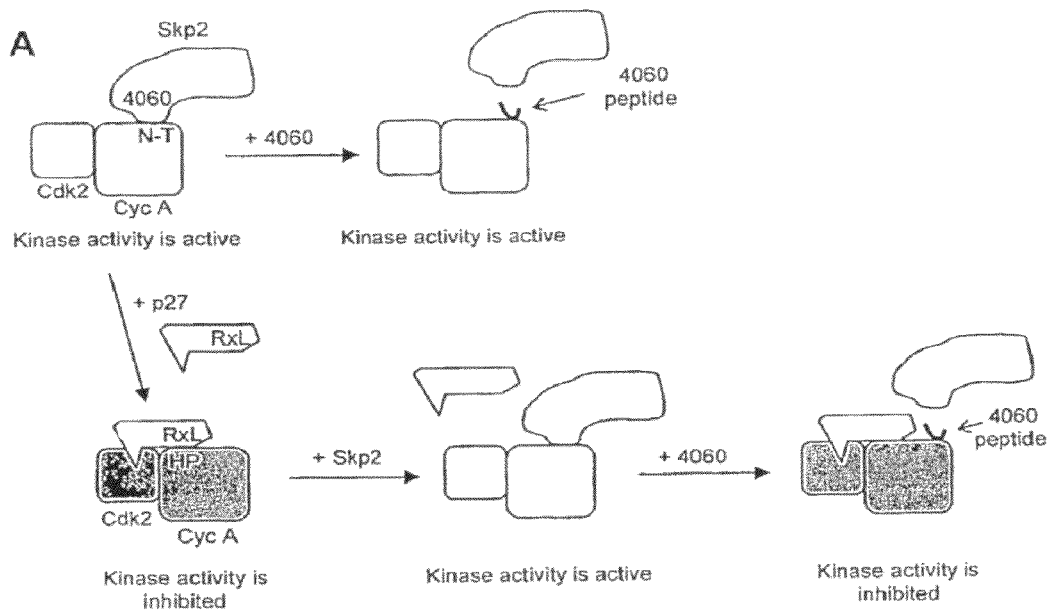
FIG. 11 is a cartoon, photographs of results of kinase reactions, and graphs showing the effects of the 4060 peptide on cyclin A/Cdk2 kinase. Panel A shows a working model for the action of the 4060 peptide in kinase reactions with purified components. Panel 13 shows in vitro kinase reactions carried out with purified cyclin A/Cdk2, with inclusion of various peptides at the indicated concentrations. GST-Rb-C was used as substrate. Panel C shows in vitro kinase reactions with purified proteins and indicated peptides at the indicated concentrations. Phosphorylation of GST-Rb-C was quantified and plotted.
Figure 11:
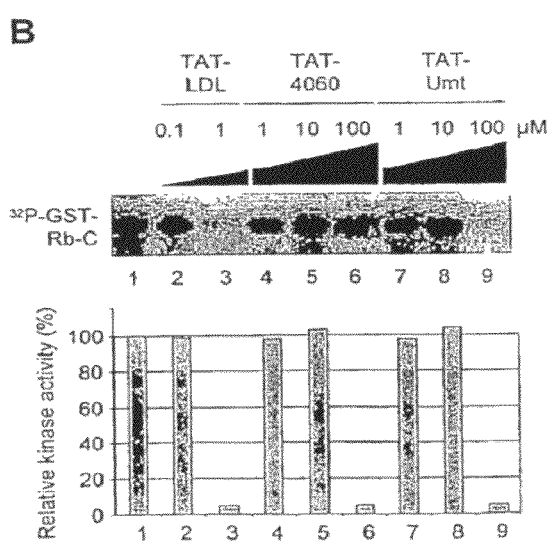
Figure 11:
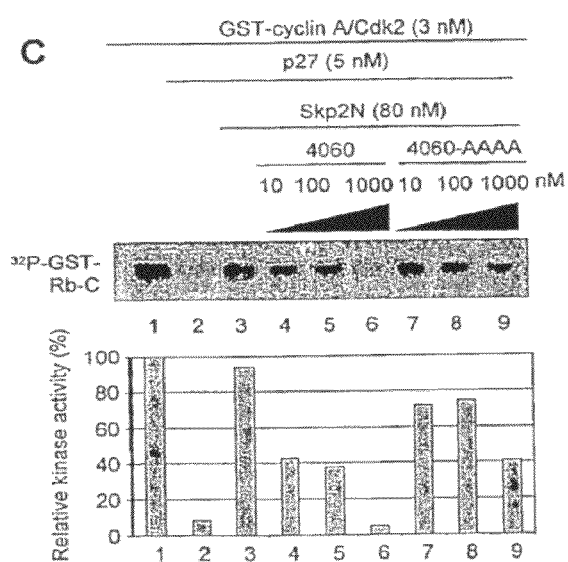

The biochemical effects of the 4060 peptide in vitro was first studied. The work described in Example 1 established that the stable interaction between Skp2 N-terminus and cyclin A N-terminus (the 4060 to N-T interaction, see FIG. 11A for a cartoon representation) is to protect cyclin A/Cdk2 from inhibition by p27 since Skp2-cyclin A interaction itself does not inhibit or stimulate cyclin A/Cdk2 kinase activity but rather competes with p27 binding to cyclin A/Cdk2. Importantly, while Skp2 binding to cyclin A is competitive and mutually exclusive with p27 binding to cyclin A, the 4060 blocking peptide does not interfere with p27-cyclin A interaction, an RxL to HP type interaction (Example 1). This difference between Skp2 and the 4060 blocking peptide in competing with p27 binding to cyclin A can be most simply explained by the small size of the 4060 peptide, and allowed the formation of a working model for the effects of 4060 peptide on cyclin A/Cdk2 kinase in a defined kinase reaction with Skp2 and p27, as presented in cartoon form in FIG. 11A.

Since Skp2 binding to cyclin A did not have inhibitory effects on its associated kinase activity, it was predicted that the 4060 peptide should likewise not inhibit cyclin A-associated kinase activity. To test this prediction, various peptides were added to an in vitro kinase reaction with purified cyclin A/Cdk2 (~3 nM concentration). An E2F1-derived RxL peptide, LDL peptide, was used for comparison since it could inhibit cyclin A/Cdk2 kinase activity (Sun et al., 2006, and see next section). Since a TAT sequence was later added to these peptides for trans-membrane delivery (see next section), two versions of each peptide (without TAT and with TAT) was used in these kinase assays. These two versions of peptides yielded identical results and therefore only presented results with one version of the peptides. As shown in FIG. 11B, addition of 1 µM TAT-LDL peptide caused a ten-fold inhibition of cyclin A/Cdk2 kinase activity towards the GST-Rb-C substrate, as expected (Sun et al., 2006). In comparison, the TAT-4060 peptide, like a negative control peptide (TAT-Umt, Sun et al., 2006), did not show inhibitory effect at 1 µM and 10 µM concentrations. Both TAT-4060 and TAT-Umt reproducibly slightly increased the kinase activity although these effects were unlikely to be significant. At 100 µM concentration, both TAT-4060 and TAT-Umt caused significant inhibition of cyclin A/Cdk2 kinase activity, indicating that at very high concentrations these peptides could non-specifically inhibit cyclin A/Cdk2 kinase activity. These results reveal a further distinction between Skp2-cyclin A interaction and interactions mediated by the RxL motif.

The effects of the 4060 peptide on cyclin A/Cdk2 kinase activity in the presence of Skp2 and p27 were then determined. Consistent with the results described in Example 1, p27 (5 nM) inhibited cyclin A/Cdk2 (3 nM) kinase activity by ten-fold, which was completely reversed by Skp2N (80 nM), demonstrating the protective effect of Skp2 on cyclin A/Cdk2 against the inhibitory effects of p27 (FIGS. 11A and C, lanes 1, 2, and 3). As predicted in the working model, inclusion of the 4060 blocking peptide abolished this protective effect in a dose-dependent manner (lanes 4 to 6). A derivative peptide containing alanine substitutions at four conserved residues and ineffective in blocking Skp2-cyclin A interaction (the 4060AAAA peptide, Example 1) was much weaker in disrupting the protective effect of Skp2N (lanes 7 to 9). These results demonstrate that the 4060 peptide can inhibit cyclin A/Cdk2 kinase activity when Skp2 and p27 are both present in the reaction. This mode of action of the 4060 peptide represents a distinct mechanism to inhibit cyclin A/Cdk2 than the functional mechanism of RxL peptides (which directly inhibits cyclin A kinase activity by blocking its access to phosphorylation substrates [Sun et al., 2006]).

Disruption of Skp2-cyclin A interaction with blocking peptide induces cell death in cancer cells but not in normal cells. To determine the effects of disrupting Skp2-cyclin A interaction in cancer cells, the HIV derived cell membrane penetration domain TAT was fused to the 4060 peptide with a glycine linker to generate the TAT-4060 peptide. TAT-Umt and TAT-4060AAAA were used as controls. Nevertheless, the possibility still formally exists that the TAT-4060 peptide may disrupt interactions between the 40-60 sequences of Skp2 and other unidentified proteins in the cell that interact with the 40-60 sequence in a manner similar to cyclin A.

Figure 12:
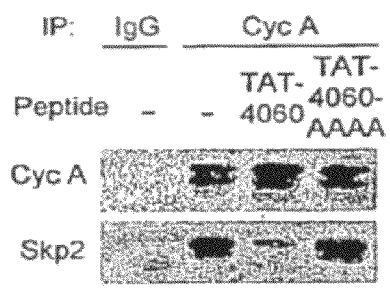
FIG. 12 is photographs of western blots and kinase assays and graphs showing the effects of trans-membrane delivery of the 4060 peptide. In Panel A, U2OS cells were treated with 50 µM of indicated peptide for twelve hours. Cell extracts were prepared for immunoprecipitation and Western blot analysis as indicated. Panel B shows the same cell extracts used in western blots as indicated. In Panel C, the same extracts were used in IP-kinase assays as indicated. The extent of phosphorylation was quantified and plotted.
Figure 12:
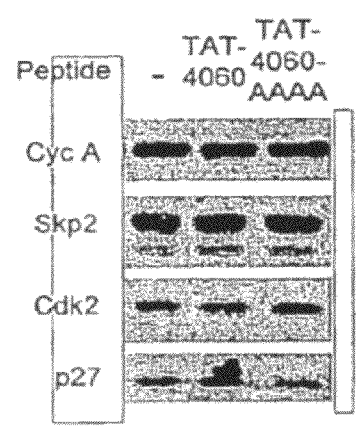
Figure 12:
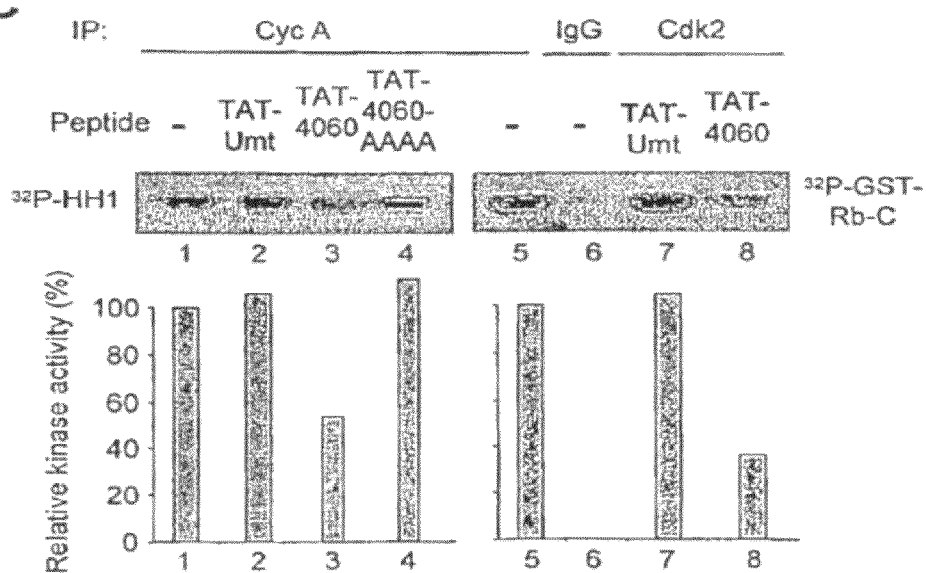

Trans-membrane delivery of TAT-4060 peptide resulted in dissociation of interaction between cellular Skp2 and cyclin A/Cdk2 as determined with coimmunoprecipitation with cyclin A (FIG. 12A). The mutant peptide TAT-4060AAAA did not have this effect. The loss of Skp2-cyclin A/Cdk2 interaction was not due to a reduction in levels of these proteins (FIG. 12B). Importantly, cellular p27 protein levels were not affected by the blocking peptide. This result provided further support that cyclin A binding to Skp2 N-terminus is not required for Skp2-mediated p27 ubiquitylation and degradation (Example 1). It also reveals a key biochemical difference between disruption of Skp2-cyclin A interaction and knockdown of Skp2 (which led to significant increases in p27 protein levels as shown in FIG. 10A). When kinase activities were determined in anti-cyclin A and anti-Cdk2 immune complexes, treatment with TAT-4060 resulted in a clear reduction of the associated kinase activity as compared with treatment with TAT-4060AAAA or TAT-Umt (FIG. 12C). Here, it is important to point out that although we used p27 as an inhibitor of cyclin A-associated kinase activity in purified kinase reactions with the 4060 blocking peptide shown in FIG. 11, the effects of blocking Skp2-cyclin A interaction on cyclin A-associated kinase activity in cells is unlikely to be mediated by p27 alone. There was no significant interaction between p27 and cyclin A in U2OS cells before and after treatment of TAT-4060. p27 family members p21 and p57, and the pocket proteins p107 and p130 (Adams et al., 1996) may bind and inhibit cyclin A-associated kinase activity through the RxL-HP interaction mechanism. More studies are needed to determine which of these proteins, or combinations of these proteins, are responsible for inhibition of cyclin A-associated kinase activity when Skp2-cyclin A interaction was blocked by TAT-4060.

The biological effects of TAT-4060 was next determined. TAT-LDL was used for comparison. Sequence of LDL (PVKRRLDL—SEQ ID NO:11) is derived from the N-terminus of E2F1 that mediates E2F1-cyclin A interaction. This interaction facilitates phosphorylation of E2F1 by cyclin A/Cdk2, which Inhibits DNA binding and transactivation activity of the E2F1/DP1 dimer (Castane et al., 1998). Since E2F1 can induce apoptosis, this function of cyclin A/Cdk has been shown to play a survival role in cancer cells (Krek et al., 1994), and TAT-LDL has been shown to induce cancer cell death (Krek et al., 1995).

Figure 13:
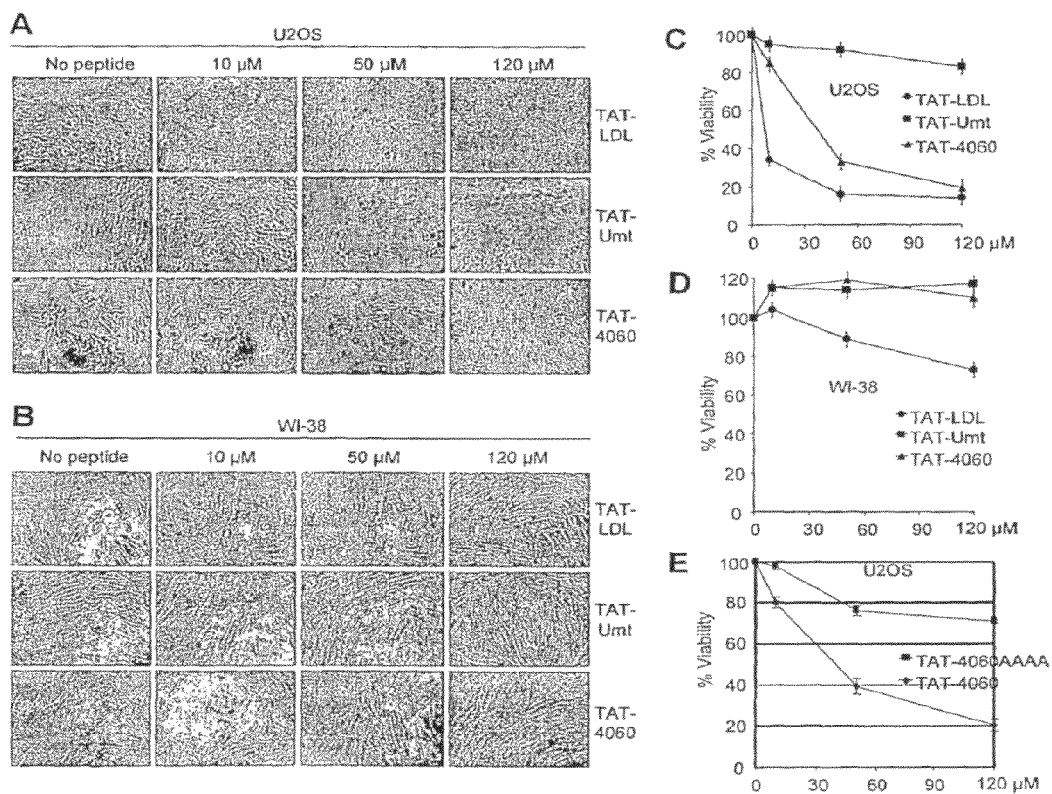
FIG. 13 is micrographs and graphs showing cancer cell-selective killing by TAT-4060. In Panels A and B, U2OS and WI38 cells were treated with the indicated peptides at the indicated concentrations for 24 hours and then photographed at 10× magnification. Panels C and D show quantitative analysis of the results shown in Panels A and B by MTS assay in triplet wells. In Panel E the mutant peptide TAT-4060AAAA was tested in the cell killing assay as in Panel C.

As shown in FIGS. 13A and C, TAT-4060 induced significant cell death in U2OS cells to similar degrees as TAT-LDL at twenty four hours after the addition of peptides to cell culture media. Also like TAT-LDL, TAT-4060 did not affect human diploid fibroblasts WI-38 (FIGS. 13B and D). As a negative control, TAT-Umt did not have cell killing effects in either cell lines at the same concentrations. TAT-4060AAAA also did not have significant cell killing effects (FIG. 13E). These results suggest that the cancer cell killing effects of TAT-4060 were a specific activity of this peptide correlated with its ability to block Skp2-cyclin A interaction. In comparison, both TAT-Umt and TAT-4060 inhibited cyclin A/Cdk2 kinase activity in vitro at peptide concentrations of 100 μM (FIG. 11B). It is currently unknown how peptide concentrations in the culture media translate into intro-cellular peptide concentrations. It is believed that the ability of TAT-4060 to inhibit cyclin A kinase activity in vitro at 100 μM concentration was unlikely to be the cause of its cancer cell killing effects, since TAT-Umt inhibited cyclin A kinase activity in vitro at 100 μM but did not exhibit cell killing effects at 120 μM. TAT-LDL or TAT-4060-treated U2OS cells showed condensed nuclear morphology indicative of apoptosis (data not shown), but the molecular mechanisms of cell killing by TAT-4060 and TAT-LDL remain to be determined. TAT-LDL exhibited higher potency at $IC_{50}$ (7.5 μM for TAT-LDL and 35 μM for TAT-4060). In comparison, TAT-4060 showed higher specificity between U2OS and WI-38 cells (TAT-LDL killed 25% of WI-38 cells at 120 μM while TAT-4060 and TAT-Umt had no effect). These results document that inhibiting Skp2-cyclin A interaction can lead to a significantly different therapeutic effect than knocking down Skp2 in U2OS cells (see Discussion).

TAT-4060 peptide can synergize with TAT-LDL peptide in killing cancer cells. Combinatorial therapies that target two or more distinct mechanisms of common or related pathways often provide an effective means to increase therapeutic efficacy. Identification of a new mechanism to inhibit cyclin A/Cdk2 kinase activity and to kill cancer cells by TAT-4060 prompted the determination of whether there was a synergistic relationship between TAT-4060 and TAT-LDL.

Figure 14:
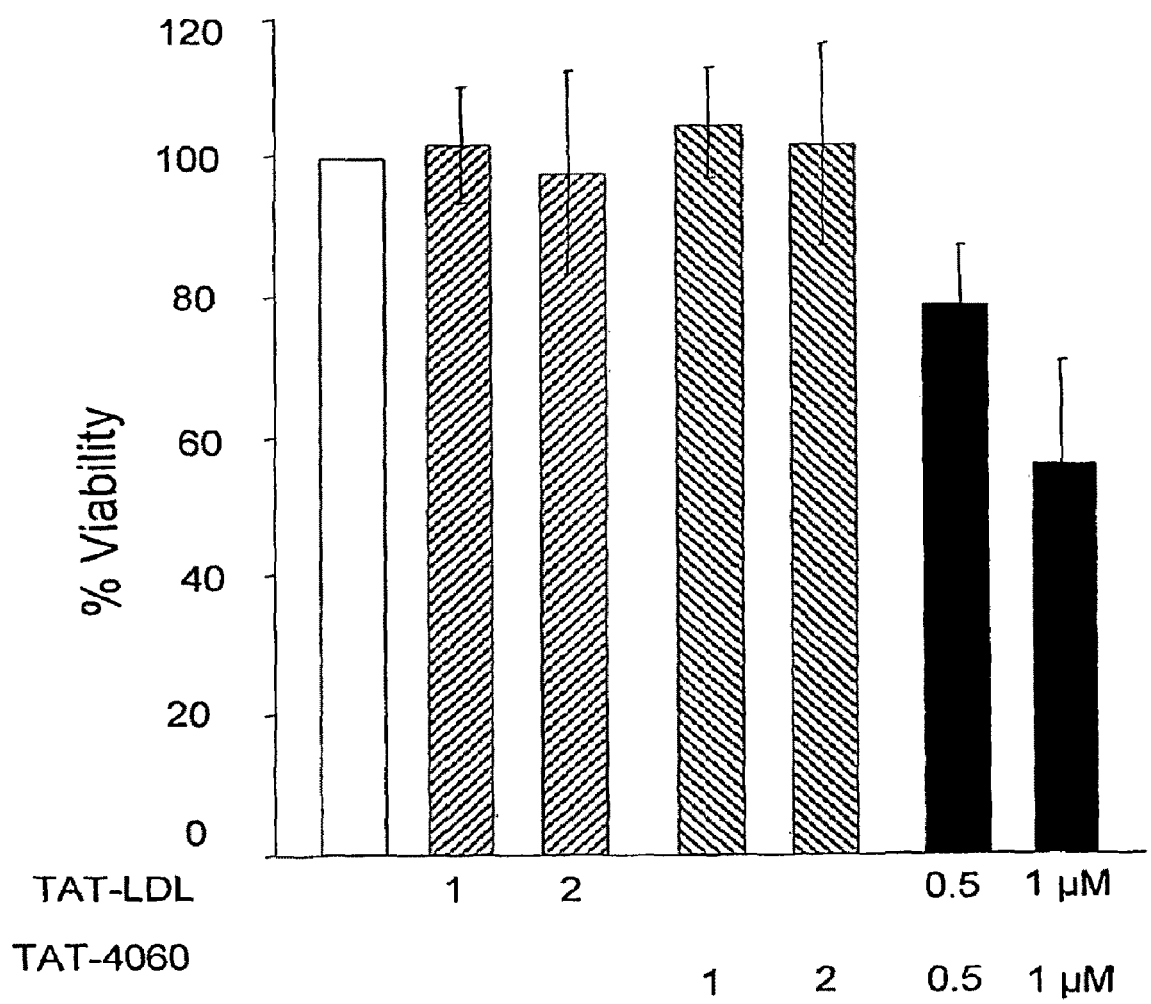
FIG. 14 is a graph showing synergy between TAT-4060 and TAT-LDL. U2OS cells were treated with indicated concentrations of the indicated peptides for 24 hours and MTS assays were performed to determine cell viability as in FIG. 13.

As shown in FIG. 14, when used at 1 or 2 μM concentrations, neither TAT-LDL nor TAT-4060 exhibited any cell killing effects since these concentrations were well below the $IC_{50}$ of these peptides. However, at a combined concentration of 1 μM (0.5 μM TAT-4060 and 0.5 μM TAT-LDL), TAT-4060 and TAT-LDL together already showed clear cell killing effects. At a combined concentration of 2 μM, these two peptides killed more than 40% of the cells. This significant synergy between TAT-LDL and TAT-4060 is consistent with these two peptides killing U2OS cells through different mechanisms and reveals a significant clinical value for these two potential targeted therapeutics.

Figure 15:
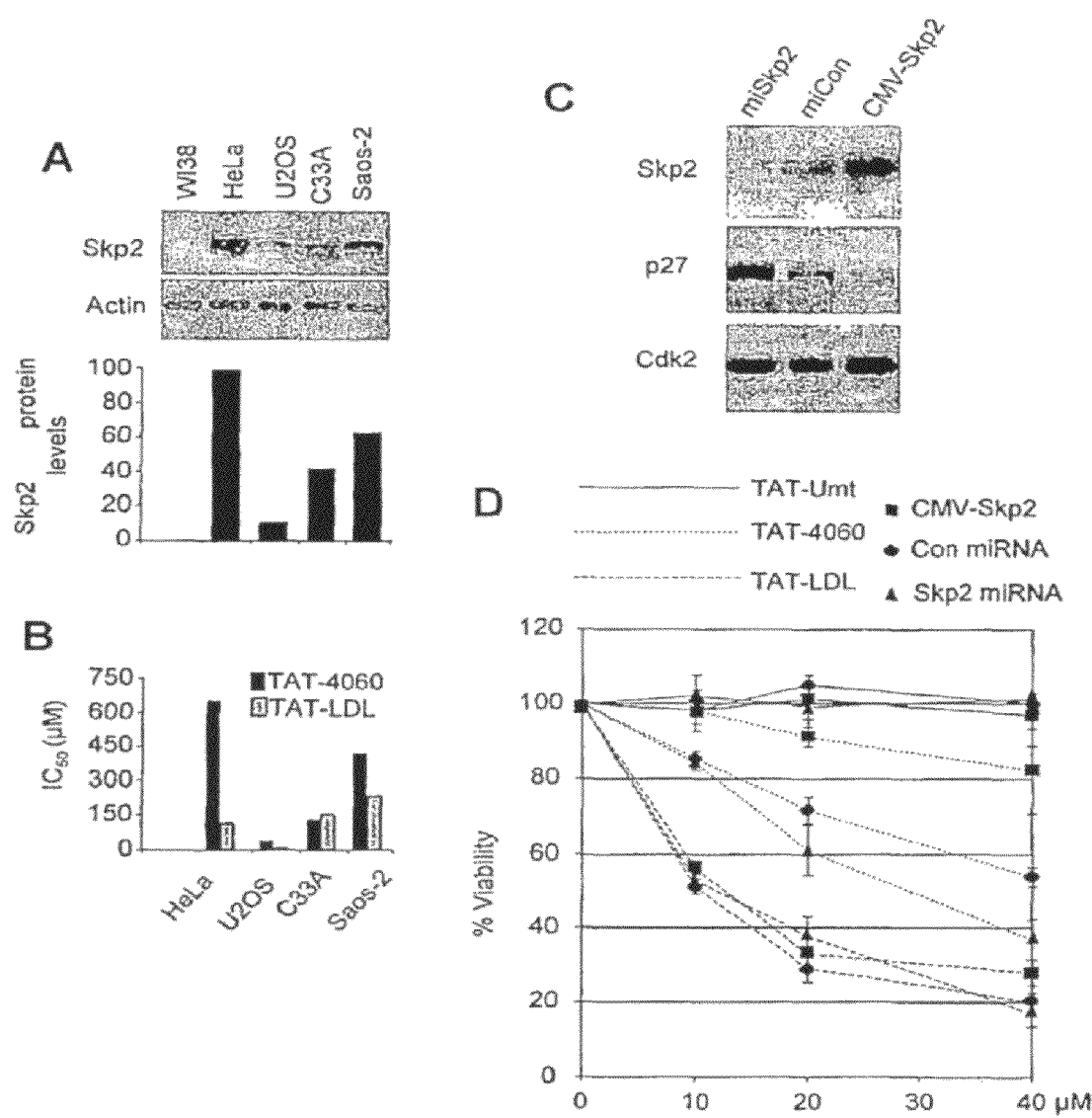
FIG. 15 is photographs of western blots and graphs showing the correlation between Skp2 levels and the $IC_{50}$ of TAT-4060. In Panel A cellular Skp2 levels were analyzed by Western blot with actin as loading control. The film was scanned and quantified for plotting relative Skp2 protein levels. In Panel B, the IC50 of TAT-4060 and TAT-LDL in different cancer cell lines were plotted. Panel C shows western blots of U2OS cell lysates two days after infection with lentiviruses expressing Skp2 miRNA, control miRNA, or exogenous Skp2, as indicated. In Panel D various U2OS cells were treated with indicated concentrations of indicated peptides for 24 hours. Cell viability was determined with MTS assays as in FIG. 13.

$IC_{50}$ of the 4060 peptide positively correlates with Skp2 protein abundance in cancer cells. Skp2 is frequently overexpressed at various levels in various cancer cells. If TAT-4060 kills cancer cells by disrupting Skp2-cyclin A interaction, higher peptide concentrations should be needed to kill cancer cells with higher levels of Skp2. In comparison, since TAT-LDL is believed to kill cancer cells by blocking access of cyclin A to E2F1, there need not be a direct correlation between effective TAT-LDL concentrations and cellular Skp2 protein levels. To test this prediction, Skp2 protein levels and $IC_{50}$ of both TAT-4060 and TAT-LDL was determined for the panel of four cancer cell lines. As shown in FIGS. 15A and B, an unbroken correlation between Skp2 protein levels and $IC_{50}$ was indeed observed for TAT-4060, but not for TAT-LDL. Here, it is important to point out that for cancer cells with high levels of Skp2 such as HeLa cells, cell killing required very high concentrations of TAT-4060 peptide, which may induce non-specific cytotoxic effects.

Whether artificial manipulation of Skp2 protein levels in U2OS cells could change the $IC_{50}$ of various peptides was also investigated. Skp2 protein levels were reduced by knockdown and increased by overexpression from a CMV based expression vector as shown in FIG. 15C. Results shown in FIG. 15D demonstrate that artificial decrease in Skp2 protein levels in U2OS cells reduced the concentrations of TAT-4060 peptide to achieve 40% killing from 40 μM to 20 μM, while artificial increase of Skp2 protein levels rendered TAT-4060 nearly as ineffective as TAT-Umt. In the same experiments, effects of TAT-LDL and TAT-Umt were not affected by Skp2 knockdown or overexpression. Together, these results suggest that the effectiveness of TAT-4060 in killing cancer cells could be predicted by the abundance of its intended target, which is an expected and valuable property of a targeted therapeutics.

Discussion

In addition to functioning as a substrate-recruiting subunit of $SCF^{Skp2}$-Roc1 E3 ubiquitin ligase targeting p27 for ubiquitylation, Skp2 forms stable complex with cyclin A/Cdk2 to protect it from inhibition by p27 (Example 1). In this study, the functional consequences of the Skp2-cyclin A interaction was investigated using an interaction-blocking peptide. In kinase reactions with purified proteins, this blocking peptide (the 4060 peptide) did not itself specifically (at concentrations up to 10 μM) inhibit cyclin A/Cdk2 kinase but could do so when cyclin A/Cdk2 was protected by Skp2 in the presence of p27. Trans-membrane delivery of this blocking peptide exhibited cancer cell killing effects while efficient knockdown of Skp2 only had mild inhibitory effects on proliferation for the four cancer cell lines tested. These results demonstrate that disrupting Skp2-cyclin A interaction could be a more effective strategy than knocking down Skp2 in targeting Skp2 for therapeutic intervention in the treatment of cancer.

At the same time, these results also raise an obvious question: why do knockdown of Skp2 and disruption of Skp2-cyclin A interaction have distinctive effects on these cancer cells (since knockdown of Skp2 should also abolish the Skp2-cyclin A interaction)? Limitations and differences of the technologies used for these two approaches should first be considered. Since RNAi mediated gene knockdown cannot be equated with gene knockout, it is possible that a more complete Skp2 knockout in cancer cells may induce a cell killing effect. It is also possible that the 4060 blocking peptide induced cancer cell killing through mechanisms in addition to dissociating Skp2-cyclin A interaction. The kinetics of action is also different between RNAi mediated gene knockdown and trans-membrane delivery of blocking peptides. While these possibilities remain to be addressed, we believe that results of this study may reflect important functional properties of the Skp2-cyclin A interaction and provide new insights into this aspect of Skp2 function.

A salient feature of Skp2-cyclin A interaction is that Skp2 interacts with sequences in the N-terminus of cyclin A (Example 1) and is therefore specific for cyclin A since sequences in cyclin A N-terminus are not conserved in other cyclins. This contrasts with the RxL-PH type interaction since HP is present in all cyclins. Since the biochemical significance of Skp2-cyclin A interaction is to protect cyclin A from inhibition by p27 (and possibly by other RxL type inhibitors), the absolute specificity for cyclin A implies that protecting cyclin A is more important than protecting multiple cyclins together. It follows that specifically inhibiting cyclin A alone may be more detrimental to cancer cells than non-specifically inhibiting multiple cyclins due to the creation of an imbalance between cyclin A-associated kinase activity and kinase activities associated with other cyclins. This scenario in fact is consistent with a number of previous findings. Elimination of Cdk2, which would inhibit kinase activities associated with cyclin A and cyclin E, did not have cancer cell killing effects (Chen et al., 1999; Tetsu and Mccormick, 2003) while elimination of cyclin A/Cdk2 complex could cause cancer cell death (Tetsu and Mccormick, 2003).

In this respect, it is interesting that the ubiquitylation activity of Skp2 has positive regulatory effects on multiple cyclins since ubiquitylation target p27 (and also p21 and p57 to a lesser degree) inhibits multiple cyclins with the RxL-HP interaction mechanism. This may explain why knockdown of Skp2 and the accompanying increases in p27 did not cause cell death in the four cancer cell lines. A dual-role of Skp2 in targeting p27 for degradation and specifically protecting cyclin A associated kinases may be selected for in tumorigenesis to maximize its oncogenic activity by promoting general proliferation and ensuring cancer cell survival at the same time. Accordingly, specifically inhibiting the cyclin A binding activity of Skp2 may represent an effective strategy of targeting Skp2 and this study provides the experimental evidence and a drug candidate for further development of this new paradigm of targeting Skp2 for cancer treatment.

Materials and Methods

Skp2 Knockdown and overexpression. The target sequences for Skp2 knockdown are 5'-CCTTAGACCTCA-CAGGTAA-3' (SEQ ID NO:12) and 5'-CAGTCGGTGC-TATGATATA-3' (SEQ ID NO:13). The negative control is an irrelevant sequence (5'-GTTACAAAGCAGAAGTTAA-3' [SEQ ID NO:14], which is derived from the 3' untranslated region of mouse p27 and does not match any human sequence in the data bases). Construction of lentivirus-based multi-miRNA hairpin constructs, production of lentivirus, and infection with lentivirus were previously described (Chen et al., 2004). Overexpression of Skp2 was achieved by transduction with a lentivirus expressing a flag-tagged Skp2 expressed from a CMV promoter. Cell lines U2OS, HeLa, C33A, and Saos2 were maintained in standard conditions.

Antibodies, peptides and treatment of cells with cell permeable peptides. Antibodies to Actin (C-2), Cdk2 (M-2) and cyclin A (H-432) were from Santa Cruz. Anti-cyclin A (E23) was obtained from NeoMarkers. Anti-p27 (K25020) was from Transduction laboratories. Anti-Skp2 (51-1900 and 32-3300) was purchased form Zymed. The following peptides were custom ordered from Genescript. 4060 (KTSELL-SGMGVSALEKEE) (SEQ ID NO:3), 4060AAAAA (KT-SEAASGMGVAAAEKEE) (SEQ ID NO:10), TAT-4060 (YGRKKRRQRRRGKTSELLSGMGVSALEKEE) (SEQ ID NO:15), TAT-4060AAAA (YGRKKRRQRRRGKT-SEAASGMGVAAAEKEE) (SEQ ID NO:16), TAT-LDL (YGRKKKRRQRRRGPVKRRLDL) (SEQ ID NO:17), TAT-Umt (YGRKKRRQRRRGETDHQYLAESS) (SEQ ID NO:18). Western blotting, immunoprecipitation, kinase assays, FACS. These were all performed as described in Example 1.

Cell proliferation and survival assays. For the cell proliferation assay shown in FIG. 10D, $1 \times 10^4$ cells were plated in each well of 24 well plates and allowed to grow for a course of four days in the presence of 10% FBS. Cell numbers were counted every day from triplet wells. For cell survival assays in FIGS. 13, 14 and 15, $1 \times 10^3$ cells were plated in each well of 96 well plates and allowed to adhere overnight in the presence of 10% FBS. The cells were washed once with Opti-MEM (GIBCO) followed by incubation with different concentrations of peptides in Opti-MEM for 24 hours in triplicate. MTS assay was then performed following manufacturer's protocol (Promega).

The above Examples show the molecular, biochemical, and biological significance of the Skp2-cyclin A interaction. The Skp2-cyclin A interaction represents both a new mechanism of Skp2 function, which is critical for cancer cell survival, and a new mechanism of positively regulating cyclin A/Cdk kinase activity, which is effectively exploited during tumorigenesis in the context of Skp2 overexpression. The demonstration that the Skp2-cyclin A interaction-blocking peptide can induce cancer cell death in synergy with the LDL peptide provides a new compound to target cyclin A function for mechanism-based cancer cell-selective therapeutics.

REFERENCES

Adams, P. D., Sellers, W. R., Sharma, S. K., Wu, A. D., Nallin, C. M. and Kaelin, J. W. G. (1996) Identification of a cyclin-cdk2 recognition motif present in substrates and p21-like cyclin-dependent kinase inhibitors. *Mol. Cell. Biol.*, 16, 6623-6633.

Bai, C., Sen, P., Hofmann, K., Ma, L., Goebl, M., Harper, J. W. and Elledge, S. J. (1996) SKP1 connects cell cycle regulators to the ubiquitin proteolysis machinery through a novel motif, the F-box. *Cell*, 86, 263-274.

Bashir, T., Dorrello, N. V., Amador, V., Guardavaccaro, D. and Pagano, M. (2004) Control of the SCF(Skp2-Cks1) ubiquitin ligase by the APC/C(Cdh1) ubiquitin ligase. *Nature*, 428, 190-193.

Ben-Izhak, O., Lahav-Baratz, S., Meretyk, S., Ben-Eliezer, S., Sabo, E., Dirnfeld, M., Cohen, S. and Ciechanover, A. (2003) Inverse relationship between Skp2 ubiquitin ligase and the cyclin dependent kinase inhibitor p27Kip1 in prostate cancer. *J. Urol.*, 170, 241-245.

Bornstein, G., Bloom, J., Sitry-Shevah, D., Nakayama, K., Pagano, M. and Hershko, A. (2003) Role of the SCFSkp2 ubiquitin ligase in the degradation of p21Cip1 in S phase. *J. Biol. Chem.*, 278, 25752-25757.

Bourne, Y., Watson, M. H., Hickey, M. J., Holmes, W., Rocque, W., Reed, S. I. and Tainer, J. A. (1996) Crystal structure and mutational analysis of the human CDK2 kinase complex with cell cycle-regulatory protein CksHs1. *Cell*, 84, 863-874.

Cardozo T, Pagano M (2004) The SCF ubiquitin ligase: insights into a molecular machine. *Nat. Rev. Mol. Cell Biol.*, 5, 739-51.

Carrano, A. C., Eytan, E., Hershko, A. and Pagano, M. (1999) SKP2 is required for ubiquitin-mediated degradation of the CDK inhibitor p27. *Nat. Cell Biol.*, 1, 193-199.

Castano E, Kleyner Y, Dynlacht B D (1998) Dual cyclin-binding domains are required for p107 to function as a kinase inhibitor. *Mol. Cell. Biol.*, 18, 5380-91.

Chen, Y. N., S. K. Sharma, T. M. Ramsey, L. Jiang, M. S. Martin, K. Baker, P. D. Adams, K. W. Bair, and W. G. Kaelin, Jr. (1999) Selective killing of transformed cells by cyclin/cyclin-dependent kinase 2 antagonists. *Proc. Natl. Acad. Sci. USA*, 96, 4325-4329.

Chen W, Lee J, Cho S Y, Fine H A (2004) Proteasome-mediated destruction of the cyclin a/cyclin-dependent kinase 2 complex suppresses tumor cell growth in vitro and in vivo. *Cancer Res.*, 64, 3949-57.

Drobnjak, M., Melamed, J., Taneja, S., Melzer, K., Wieczorek, R., Levinson, B., Zeleniuch-Jacquotte, A., Polsky, D., Ferrara, J., Perez-Soler, R., Cordon-Cardo, C., Pagano, M. and Osman, I. (2003) Altered expression of p27 and Skp2 proteins in prostate cancer of African-American patients. *Clin. Cancer Res.*, 9, 2613-2619.

Dynlacht, B. D., O. Flores, J. A. Lees, and E. Harlow (1994) Differential regulation of E2F trans-activation by cyclin-cdk2 complexes. *Genes Dev.*, 8, 1772-1786.

Follenzi, A., Sabatino, G., Lombardo, A., Boccaccio, C. and Naldini, L. (2002) Efficient gene delivery and targeted expression to hepatocytes in vivo by improved lentiviral vectors. *Hum. Gene Ther.*, 13, 243-260.

Ganoth, D., Bornstein, G., Ko, T. K., Larsen, B., Tyers, M., Pagano, M. and Hershko, A. (2001) The cell-cycle regulatory protein Cks1 is required for SCF$^{Skp2}$-mediated ubiquitinylation of p27. *Nat. Cell Biol.*, 3, 321-324.

Hao, B., Zheng, N., Schulman, B. A., Wu, G., Miller, J. J., Pagano, M. and Pavletich, N. P. (2005) Structural basis of the Cks1-dependent recognition of p27(Kip1) by the SCF (Skp2) ubiquitin ligase. *Mol. Cell*, 20, 9-19.

Jeffrey, P. D., Russo, A. A., Polyak, K., Gibbs, E., Hurwitz, J., Massague, J. and Pavletich, N. P. (1995) Mechanism of CDK activation revealed by the structure of a cyclinA-CDK2 complex. *Nature*, 376, 313-320.

Ji, P., Jiang, H., Rekhtman, K., Bloom, J., Ichetovkin, M., Pagano, M. and Zhu, L. (2004) An Rb-Skp2-p27 pathway mediates acute cell cycle inhibition by Rb and is retained in a partial-penetrance Rb mutant. *Mol. Cell*, 16, 47-58.

Ji, P., Goldin, L., Ren, H., Sun, D., Guardavaccaro, D., Pagano, M. and Zhu, L. (2006) Skp2 contains a novel cyclin A binding domain that directly protects cyclin A from inhibition by p27$^{Kip1}$. *J. Biol. Chem*, 281, 24058-24069.

Ji, P., Sun, D., Wang, H., Bauzon, F. and Zhu, L. (2007) Disrupting Skp2-cyclin A interaction with a blocking peptide induces selective cancer cell killing. *Mol. Cancer Ther.*, 6, 684-691.

Jiang F, Caraway N P, Li R, Katz R L (2005) RNA silencing of S-phase kinase-interacting protein 2 inhibits proliferation and centrosome amplification in lung cancer cells. *Oncogene*, 24, 3409-18.

Kamura, T., Hara, T., Kotoshiba, S., Yada, M., Ishida, N., Imaki, H., Hatakeyama, S., Nakayama, K. and Nakayama, K. I. (2003) Degradation of p57Kip2 mediated by SCF-Skp2-dependent ubiquitylation. *Proc. Natl. Acad. Sci. USA*, 100, 10231-10236.

Kossatz U, Dietrich N, Zender L, et al. (2004) Skp2-dependent degradation of p27kip1 is essential for cell cycle progression. *Genes Dev.*, 18, 2602-07.

Krek, W., Ewen, M. E., Shirodkar, S. Z., Arany, Z., Kaelin, W. G. and Livingston, D. M. (1994) Negative Regulation of the growth-promoting transcription factor E2F-1 by a stably bound cyclin A-dependent protein kinase. *Cell*, 78, 161-172.

Krek, W., G. Xu, and D. M. Livingston (1995) Cyclin A-kinase regulation of E2F-1 DNA binding function underlies suppression of an S phase checkpoint. *Cell*, 83, 1149-1158.

Kudo Y, Kitajima S, Ogawa I, et al. (2005) Small interfering RNA targeting of S phase kinase-interacting protein 2 inhibits cell growth of oral cancer cells by inhibiting p27 degradation. *Mol. Cancer Ther.*, 4, 471-76.

Lee S H, Mccormick F (2005) Downregulation of Skp2 and p27/Kip1 synergistically induces apoptosis in T98G glioblastoma cells. *J. Mol. Med.*, 83, 296-307.

Lees, J. A. and R. A. Weinberg (1999) Tossing monkey wrenches into the clock: new ways of treating cancer. *Proc. Natl. Acad. Sci. USA*, 96, 4221-4223.

Lisztwan, J., Marti, A., Sutterluty, H., Gstaiger, M., Wirbelauer, C. and Krek, W. (1998) Association of human CUL-1 and ubiquitin-conjugating enzyme CDC34 with the F-box protein p45(SKP2): evidence for evolutionary conservation in the subunit composition of the CDC34-SCF pathway. *EMBO J.*, 17, 368-383.

Montagnoli, A., Fiore, F., Eytan, E., Carrano, A. C., Draetta, G. F., Hershko, A. and Pagano, M. (1999) Ubiquitination of p27 is regulated by Cdk-dependent phosphorylation and trimeric complex formation. *Genes Dev.*, 13, 1181-1189.

Nakayama, K. I. and Nakayama, K. (2005) Regulation of the cell cycle by SCF-type ubiquitin ligases. *Semin. Cell. Dev. Biol.*, 16, 323-333.

Nakayama K, Nagahama H, Minamishima Y A, et al. (2004) Skp2-Mediated Degradation of p27 regulates progression into mitosis. *Dev. Cell*, 6, 661-72.

Qin, X.-Q., D. M. Livingston, W. G. J. Kaelin, and P. Adams (1994) Deregulated transcription factor E2F-1 expression leads to S-phase entry and p53-mediated apoptosis. *Proc. Natl. Acad Sci. USA*, 91, 10918-10922.

Russo, A. A., Jeffrey, P. D., Patten, A. K., Massague, J. and Pavletich, N. P. (1996) Crystal structure of the p27Kip1 cyclin-dependent-kinase inhibitor bound to the cyclin A-Cdk2. complex. *Nature*, 382, 325-331.

Schulman, B. A., Carrano, A. C., Jeffrey, P. D., Bowen, Z., Kinnucan, E. R., Finnin, M. S., Elledge, S. J., Harper, J. W., Pagano, M. and Pavletich, N. P. (2000) Insights into SCF ubiquitin ligases from the structure of the Skp1-Skp2 complex. *Nature*, 408, 381-386.

Schulman, B. A., Lindstrom, D. L. and Harlow, E. (1998) Substrate recruitment to cyclin-dependent kinase 2 by a multipurpose docking site on cyclin A. *Proc. Natl. Acad. Sci. USA,* 95, 10453-10458.

Schwarze, S. R., K. A. Hruska, and S. F. Dowdy (2000) Protein transduction: unrestricted delivery into all cells? *Trends Cell. Biol.,* 10, 290-295.

Shan, B. and W.-H. Lee (1994) Deregulated expression of E2F-1 induces S-phase entry and leads to apoptosis. Mol. Cell. Biol. 14: 8166-8173.

Sherr, C. J. (1996) Cancer cell cycles. *Science,* 274, 1672-1677.

Sherr C J, Roberts J M (1999) CDK inhibitors: positive and negative regulators of G1-phase progression. *Genes Dev.,* 13, 1501-12.

Sitry, D., Seeliger, M. A., Ko, T. K., Ganoth, D., Breward, S. E., Itzhaki, L. S., Pagano, M. and Hershko, A. (2002) Three different binding sites of Cks1 are required for p27-ubiquitin ligation. *J. Biol. Chem.,* 277, 42233-42240.

Spruck, C., Strohmaier, H., Watson, M., Smith, A. P. L., Ryan, A., Krek, W. and Reed, S. I. (2001) A CDK-independent function of mammalian Cks1: targeting of SCF$^{Skp2}$ to the CDK inhibitor p27$^{Kip1}$. *Mol. Cell,* 7, 639-650.

Sumimoto H, Yamagata S, Shimizu A, et al. (2005) Gene therapy for human small-cell lung carcinoma by inactivation of Skp-2 with virally mediated RNA interference. *Gene Ther.,* 12, 95-100.

Sun D, Melegari M, Sridhar S, Rogler C E, Zhu L (2006) A multi-miRNA hairpin method that improves gene knockdown efficiency and provides linked multi-gene knockdown. *BioTechniques,* 41, 59-63.

Sutterluty, H., Chatelain, E., Marti, A., Wirbelauer, C., Senften, M., Muller, U. and Krek, W. (1999) p45SKP2 promotes p27Kip1 degradation and induces S phase in quiescent cells. *Nat. Cell Biol.,* 1, 207-214.

Tetsu O, Mccormick F (2003) Proliferation of cancer cells despite CDK2 inhibition. *Cancer Cell* 3, 233-45.

Tsvetkov, L. M., Yeh, K. H., Lee, S. J., Sun, H. and Zhang, H. (1999) p27Kip1 ubiquitination and degradation is regulated by the SCF$^{Skp2}$ complex through phosphorylated Thr187 in p27. *Current Biology,* 9, 661-664.

Wang, W., Ungermannova, D., Chen, L. and Liu, X. (2003) A negatively charged amino acid in Skp2 is required for Skp2-Cks1 interaction and ubiquitination of p27Kip1. *J. Biol. Chem.,* 278, 32390-32396.

Wu, X. and A. J. Levine (1994) p53 and E2F-1 cooperate to mediate apoptosis. *Proc. Natl. Acad. Sci. USA,* 91, 3602-3606.

Xiong, Y., Zhang, H. and Beach, D. (1993) Subunit rearrangement of the cyclin-dependent kinases is associated with cellular transformation. *Genes Dev.,* 7, 1572-1583.

Xu, M., K. A. Sheppard, C. Y. Peng, A. S. Yee, and H. Piwnica-Worms (1994) Cyclin A/CDK2 binds directly to E2F-1 and inhibits the DNA-binding activity of E2F-1/DP-1 by phosphorylation. *Mol. Cell. Biol.,* 14, 8420-8431.

Yam, C. H., Ng, R. W., Siu, W. Y., Lau, A. W. and Poon, R. Y. (1999) Regulation of cyclin A-Cdk2 by SCF component Skp1 and F-box protein Skp2. *Mol. Cell. Biol.,* 19, 635-645.

Yang, G., Ayala, G., De Marzo, A., Tian, W., Frolov, A., Wheeler, T. M., Thompson, T. C. and Harper, J. W. (2002) Elevated Skp2 protein expression in human prostate cancer: association with loss of the cyclin-dependent kinase inhibitor p27 and PTEN and with reduced recurrence-free survival. *Clin. Cancer Res.,* 8, 3419-3426.

Zeng, Y., E. J. Wagner, and B. R. Cullen (2002) Both natural and designed micro RNAs can inhibit the expression of cognate mRNAs when expressed in human cells. *Mol. Cell,* 9, 1327-1333.

Zhang, H., Kobayashi, R., Galaktionov, K. and Beach, D. (1995) p19Skp1 and p45Skp2 are essential elements of the cyclin A-CDK2 S phase kinase. *Cell,* 82, 915-925.

Zheng, N., Schulman, B. A., Song, L., Miller, J. J., Jeffrey, P. D., Wang, P., Chu, C., Koepp, D. M., Elledge, S. J., Pagano, M., Conaway, R. C., Conaway, J. W., Harper, J. W. and Pavletich, N. P. (2002) Structure of the Cul1-Rbx1-Skp1-F boxSkp2 SCF ubiquitin ligase complex. *Nature,* 416, 703-709.

Zhu, L., Harlow, E. and Dynlacht, B. D. (1995) p107 uses a p21$^{cIP1}$-related domain to bind cyclin/cdk2 and regulate interactions with E2F. *Genes Dev.,* 9, 1740-1752.

Zhu, X. H., Nguyen, H., Halicka, H. D., Traganos, F. and Koff, A. (2004) Noncatalytic requirement for cyclin A-cdk2 in p27 turnover. *Mol. Cell. Biol.,* 24, 6058-6066.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

APPENDIX

SEQ ID NOs

```
SEQ ID NO: 1 - combination of 4060 peptide and disclosed metazoan
peptides analogous to 4060 peptide
(KE)(TK)(SL)(EQ)(IL)L(SA)(GQ)(MA)(GK)(VR)S(AVS)L(ERG)(KS)(ED)(EKG)

SEQ ID NO: 2 - combination of 4060 peptide and disclosed vertebrate
peptides analogous to 4060 peptide
KTSELLSGMGVS(AV)L(ER)K(ED)(EK)

SEQ ID NO: 3 - 4060 peptide (derived from human Skp2 sequence
[SEQ ID NO: 8])
KTSELLSGMGVSALEKEE SEQ ID NO: 4 - 4060 peptide along with the 3 amino acids at C
terminus as in FIG. 1D
KTSELLSGMGVSALEKEEPDS
```

-continued

SEQ ID NO: 5 - mouse analog of SEQ ID NO: 4 sequence
KTSELLSGMGVSALEKEEVDS

SEQ ID NO: 6 - chicken analog of SEQ ID NO: 4 sequence
KTSELLSGMGVSVLRKDKLGN

SEQ ID NO: 7 - *Drosophila* analog of SEQ ID NO: 4 sequence
EKLQILAQAKRSSLGSEGSGN SEQ ID NO: 8 - human Skp2 amino acid sequence (GenBank AAC50242) -
the 4060 peptide sequence is in bold font
  1 mhvfktpgpa damhrkhlqe ipdlssnvat sftwgwdssk tsellsgmgv salekeepds

61 enipqellsn lghpespprk rlkskgsdkd fvivrrpkln renfpgvswd slpdelllgi 121 fsclclpell kvsgvckrwy rlasdeslwq tldltgknlh pdvtgrllsq gviafrcprs 181 fmdqplaehf spfrvqdmdl snsvievstl hgilsqcskl qnlslelrls dpivntlakn 241 snlvrlnlpg cpgfpkfplq tflsscprld elnlswcfnf tekhvqvava hvsetmtqln 301 lsgyrknlqk sdlstlvrrc pnlvhldlsn svmlkndcfq efsqlnylqh lslsrcydii 361 petllelgei ptlktlqvfg ivpdgtlqll kealphlqin cshfttiarp tignkknqei 421 wgikcrltlq kpscl SEQ ID NO: 9 - peptide RxL
SACRNLFG

SEQ ID NO: 10 - 4060AAAA
KTSEAASGMGVAAAEKEE

SEQ ID NO: 11 - peptide LDL
PVKRRLDL

SEQ ID NO: 12 - target sequence for Skp2 knockdown
CCTTAGAGCTCACAGGTAA

SEQ ID NO: 13 - target sequence for Skp2 knockdown
CAGTCGGTGCTATGATATA

SEQ ID NO: 14 - negative control - irrelevant sequence
GTTACAAAGCAGAAGTTAA

SEQ ID NO: 15 - TAT-4060
YGRKKRRQRRRGKTSELLSGMGVSALEKEE

SEQ ID NO: 16 - TAT-4060AAAA
YGRKKRRQRRRGKTSEAASGMGVAAAEKEE

SEQ ID NO: 17 - TAT-LDL
YGRKKRRQRRRGPVKRRLDL

SEQ ID NO: 18- TAT-Umt
YGRKKRRQRRRGETDHQYLAESS

What is claimed is:

1. A method of screening an agent for the ability to kill a cancer cell, the method comprising determining whether the agent inhibits Skp2-cyclin A binding by (a) combining the agent with a cyclin A and a compound comprising the sequence of SEQ ID NO:1 and which comprises from 18 to about 100 amino acids or peptidomimetics under conditions which permit the compound to bind to the cyclin A in the absence of the agent, and (b) determining whether the compound binds to the cyclin A in the presence of the agent, wherein an agent inhibits Skp2-cyclin A binding if the agent causes a reduction in binding of the compound to the cyclin A and
wherein an agent that inhibits Skp2-cyclin A binding could kill the cancer cell.

2. The method of claim 1, wherein an agent that inhibits Skp2-cyclin A binding is further tested for its ability to kill the cancer cell.

3. The method of claim 1, wherein the agent is an organic compound less than 1000 daltons.

4. The method of claim 1, wherein the peptide comprises the sequence of SEQ ID NO:3.

5. The method of claim 1, wherein the peptide consists of the sequence of SEQ ID NO:3.

6. The method of claim 1, wherein the compound is labeled with a detectible moiety.

* * * * *